United States Patent
Reddy

(10) Patent No.: US 10,646,720 B2
(45) Date of Patent: May 12, 2020

(54) PARASTERNAL PLACEMENT OF AN ACTIVE MEDICAL DEVICE USING THE INTERNAL THORACIC VASCULATURE

(71) Applicant: CARDIAC PACEMAKERS, INC., St. Paul, MN (US)

(72) Inventor: G. Shantanu Reddy, Minneapolis, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 175 days.

(21) Appl. No.: 15/801,719

(22) Filed: Nov. 2, 2017

(65) Prior Publication Data

US 2018/0133494 A1  May 17, 2018

Related U.S. Application Data

(60) Provisional application No. 62/423,638, filed on Nov. 17, 2016.

(51) Int. Cl.
| | |
|---|---|
| *A61N 1/375* | (2006.01) |
| *A61N 1/05* | (2006.01) |
| *A61N 1/362* | (2006.01) |
| *A61N 1/39* | (2006.01) |
| *A61B 17/34* | (2006.01) |
| *A61N 1/372* | (2006.01) |
| *A61N 1/368* | (2006.01) |

(52) U.S. Cl.
CPC ...... *A61N 1/37516* (2017.08); *A61B 17/3468* (2013.01); *A61N 1/05* (2013.01); *A61N 1/0563* (2013.01); *A61N 1/362* (2013.01); *A61N 1/0573* (2013.01); *A61N 1/0592* (2013.01); *A61N 1/368* (2013.01); *A61N 1/3627* (2013.01); *A61N 1/37288* (2013.01); *A61N 1/37518* (2017.08); *A61N 1/39622* (2017.08)

(58) Field of Classification Search
CPC ........ A61N 1/05; A61N 1/0563; A61N 1/362; A61N 1/37516; A61N 1/375; A61N 1/366; A61N 1/3621; A61N 1/3956; A61B 17/3468
See application file for complete search history.

(56) References Cited

U.S. PATENT DOCUMENTS

| | | |
|---|---|---|
| 6,721,597 B1 | 4/2004 | Bardy et al. |
| 6,909,917 B2 | 6/2005 | Woods et al. |

(Continued)

OTHER PUBLICATIONS

Ghosh et al., "A rare malposition of the thoracic venuous catheter introduced via the left internal jugular", Indian Journal of Critical Care Medicine, 12 (4) : 201-203, Oct.-Dec. 2008.

(Continued)

*Primary Examiner* — Tuan V Nguyen
(74) *Attorney, Agent, or Firm* — Seager, Tufte & Wickhem LLP

(57) ABSTRACT

Implantation of a cardiac stimulus system using parasternal access to the ITV is provided. Superior access may be achieved using parasternal locations in the upper ribcage to access the ITV. Inferior access may be achieved using parasternal locations in the lower ribcage to access the ITV. Parasternal access may include creating an opening in an intercostal space between two ribs and advancing a needle using ultrasound guidance.

20 Claims, 22 Drawing Sheets

(56) References Cited

U.S. PATENT DOCUMENTS

| | | | |
|---|---|---|---|
| 7,149,575 B2 | 12/2006 | Ostroff et al. | |
| 7,783,340 B2 | 8/2010 | Sanghera et al. | |
| 8,005,543 B2 | 8/2011 | Libbus et al. | |
| 8,157,813 B2 | 4/2012 | Ko et al. | |
| 8,483,841 B2 | 7/2013 | Sanghera et al. | |
| 8,483,843 B2 | 7/2013 | Sanghera et al. | |
| 2005/0043765 A1* | 2/2005 | Williams | A61N 1/057 607/9 |
| 2012/0029335 A1* | 2/2012 | Sudam | A61N 1/05 600/374 |
| 2015/0290467 A1* | 10/2015 | Ludwig | A61N 1/3962 607/4 |
| 2016/0256692 A1 | 9/2016 | Baru | |
| 2017/0021159 A1 | 1/2017 | Reddy et al. | |
| 2017/0112399 A1 | 4/2017 | Brisben et al. | |
| 2017/0113040 A1 | 4/2017 | Brisben et al. | |
| 2017/0113050 A1 | 4/2017 | Brisben et al. | |
| 2017/0113053 A1 | 4/2017 | Brisben et al. | |
| 2018/0036527 A1 | 2/2018 | Reddy et al. | |
| 2018/0036547 A1 | 2/2018 | Reddy | |
| 2018/0133462 A1 | 5/2018 | Reddy | |
| 2018/0133463 A1 | 5/2018 | Reddy | |
| 2018/0133494 A1 | 5/2018 | Reddy | |
| 2018/0169384 A1 | 6/2018 | Reddy et al. | |
| 2018/0169425 A1 | 6/2018 | Reddy et al. | |
| 2018/0178018 A1 | 6/2018 | Reddy et al. | |
| 2018/0178019 A1 | 6/2018 | Reddy et al. | |
| 2018/0193060 A1 | 7/2018 | Reddy et al. | |
| 2018/0214686 A1 | 8/2018 | De Kock et al. | |
| 2018/0256890 A1 | 9/2018 | Fuhs et al. | |
| 2018/0264270 A1 | 9/2018 | Koop et al. | |
| 2018/0296824 A1 | 10/2018 | De Krock et al. | |
| 2018/0325480 A1 | 11/2018 | Liu et al. | |
| 2018/0344200 A1 | 11/2018 | Thakur et al. | |
| 2018/0344252 A1 | 11/2018 | An et al. | |

OTHER PUBLICATIONS

Loukas et al., "The clinical anatomy of the internal thoracic veins", Folia Morphol. 66 (1): 25-32, 2007.

Moeinipour et al., "A rare central venous catheter malposition : a case report". Anesth pain Med, 4 (1):e16049, 3 pages, Feb. 2014.

Shuder et al., "Experimental Ventricular Defibrillation with an automatic and completely implanted system", Trans. Amer. Soc. Artif. Int. Organs, vol. XVI, 1970.

Shuder, "The role of an engineering oriented medical research group in developing improved methods and devices for achieving ventricular defibrillation : the University of Missouri experience," PACE , 16 (part 1): 95-124, Jan. 1993.

Advisory Action Before the Filing of an Appeal Brief for U.S. Appl. No. 15/667,167, dated Mar. 21, 2019.

Final Office Action for U.S. Appl. No. 15/667,167, dated Jan. 10, 2019.

Non-Final Office Action for U.S. Appl. No. 15/667,167, dated Jun. 26, 2018.

Non-Final Office Action for U.S. Appl. No. 15/667,167, dated Aug. 7, 2019.

Final Office Action for U.S. Appl. No. 15/667,221, dated Apr. 11, 2019.

Non-Final Office Action for U.S. Appl. No. 15/667,221, dated Oct. 1, 2018.

Notice of Allowance and Fees Due for U.S. Appl. No. 15/667,221, dated Jul. 11, 2019.

Amendment for U.S. Appl. No. 15/667,167, dated Sep. 17, 2018.

Amendment for U.S. Appl. No. 15/667,167, dated Oct. 9, 2019.

Amendment After Final Office Action for U.S. Appl. No. 15/667,167, dated Mar. 11, 2019.

Request for Continued Examination (RCE) for U.S. Appl. No. 15/667,167, dated Apr. 10, 2019.

Amendment for U.S. Appl. No. 15/667,221, dated Dec. 21, 2018.

Amendment After Final Office Action for U.S. Appl. No. 15/667,221, dated May 22, 2019.

* cited by examiner

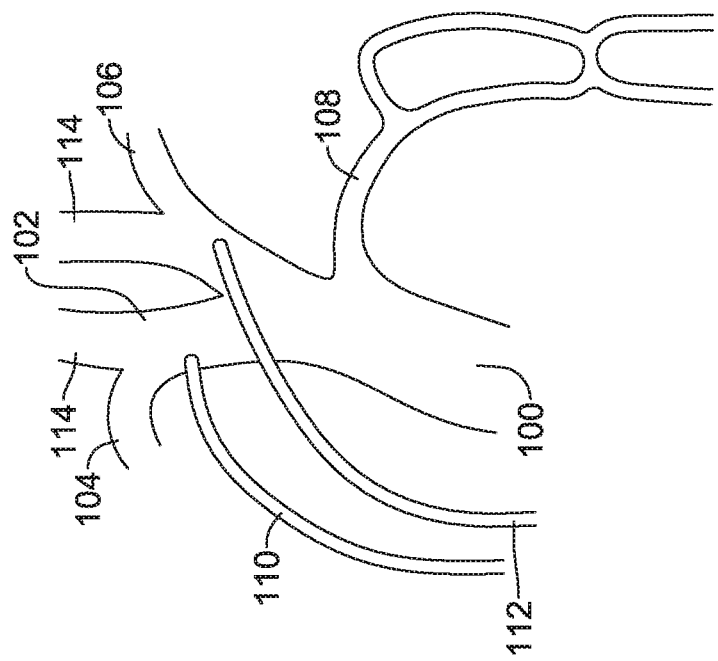
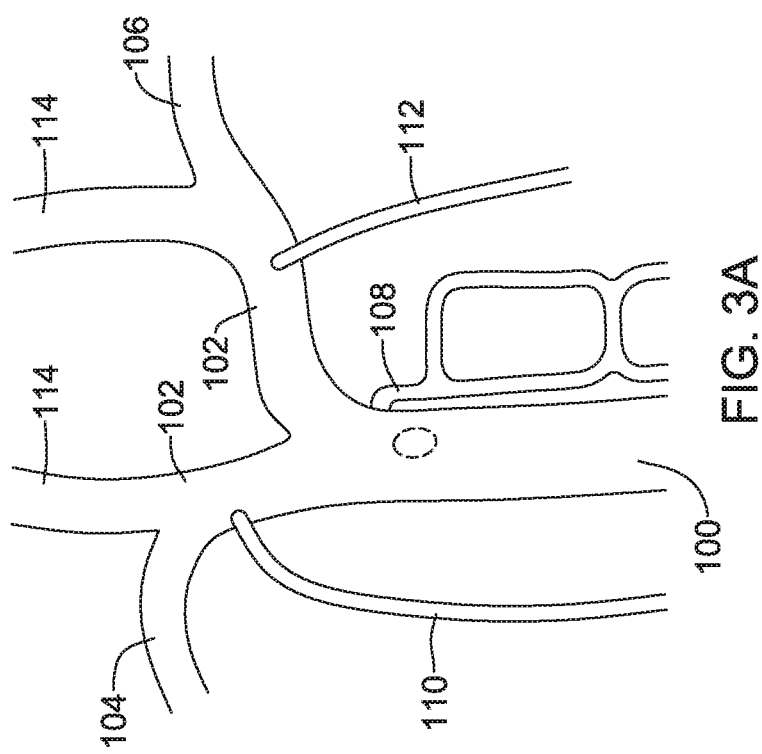
FIG. 3A
FIG. 3B

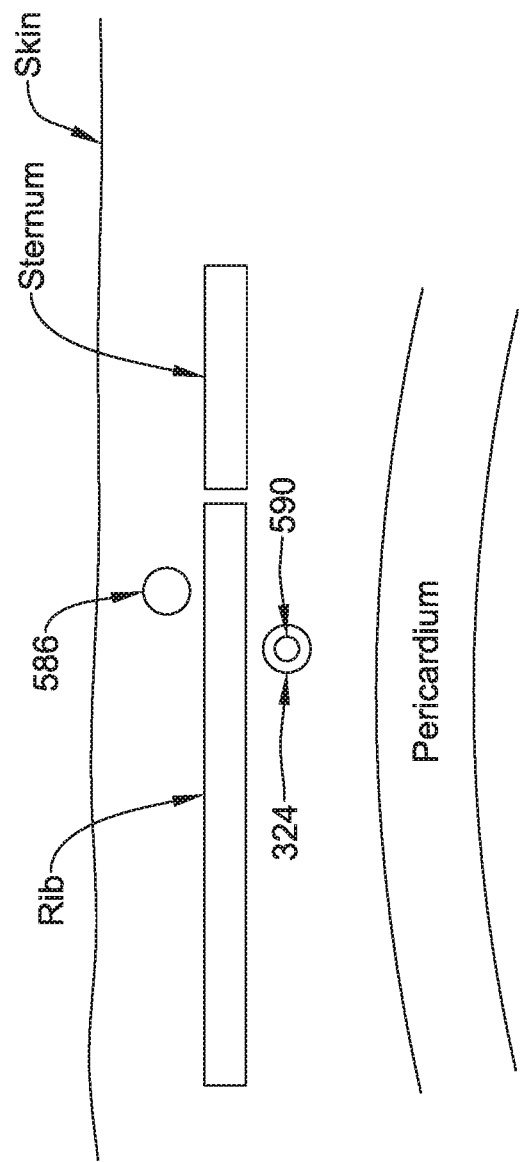

PARASTERNAL PLACEMENT OF AN ACTIVE MEDICAL DEVICE USING THE INTERNAL THORACIC VASCULATURE

CROSS REFERENCE TO RELATED APPLICATIONS

The present application claims the benefit of and priority to U.S. Provisional Patent Application Ser. No. 62/423,638, filed Nov. 17, 2016, titled PARASTERNAL PLACEMENT OF AN ACTIVE MEDICAL DEVICE USING THE INTERNAL THORACIC VASCULATURE, the disclosure of which is incorporated herein by reference.

BACKGROUND

The implantable defibrillator has been demonstrated to extend patient lives by treatment of potentially deadly arrhythmias. Over time, various efforts have been made to address complications associated with implantation of such devices. For example, early devices generally used epicardial patch electrodes implanted via thoracotomy, with attendant surgical risks and significant risks of failure of the epicardial patch electrodes and associated leads. The use of transvenous leads represented a major advance, avoiding the thoracotomy and improving reliability. However, lead failure remained a significant issue, as the lead attachment in the heart cause the lead to flex with each heartbeat. The advent of subcutaneous defibrillators allows avoidance of these lead failure issues, with leads implanted beneath the skin and over the ribcage of the patient and not subjected to the repeated flexing.

However, subcutaneous defibrillators require higher energy for defibrillation, causing the pulse generators for such systems to be larger than their transvenous predecessors, and both bradycardia pacing and anti-tachycardia pacing to avoid high voltage shock for certain conditions are of limited utility as such pacing subcutaneously can be very uncomfortable for the patient. This has led to interest in further alternative locations for implantable defibrillators, and for other medical devices such as the implantable pacemaker.

OVERVIEW

The present inventors have recognized, among other things, that the internal thoracic vasculature including, in particular, the internal thoracic vein (ITV), sometimes also referred to as the internal mammary vein, presents an opportunity for an additional alternative implant location. A lead for an implantable cardiac device may be implanted into one or both ITVs.

A first non-limiting example takes the form of a method of implanting a lead for use in a cardiac stimulus system in a patient, the lead having at least one electrode thereon; the method comprising inserting the lead parasternally into an internal thoracic vein (ITV) to a desired parasternal location relative to the heart of a patient.

Additionally or alternatively a second non-limiting example takes the form of a method as in the first non-limiting example further comprising establishing parasternal access to the ITV through an intercostal space between two ribs including inserting a needle into one of the ITV through the intercostal space, advancing a sheath into the intercostal space and into the ITV, and wherein the step of inserting the lead comprises advancing the distal end of the lead through the sheath and into the ITV.

Additionally or alternatively a third non-limiting example takes the form of a method as in the first non-limiting example further comprising establishing parasternal access to the ITV through an intercostal space between two ribs including making an incision through the patient's skin and accessing the ITV, making an incision into the ITV, and wherein the step of inserting the lead comprises advancing the distal end of the lead through the incision and into the ITV.

Additionally or alternatively a fourth non-limiting example takes the form of a method as in the second or third non-limiting example wherein the step of advancing the distal end of the lead through the sheath and into the ITV comprises advancing the distal end of the lead in an inferior direction into the ITV.

Additionally or alternatively a fifth non-limiting example takes the form of a method as in the second or third non-limiting example, wherein the step of advancing the distal end of the lead through the sheath and into the ITV comprises advancing the distal end of the lead in a superior direction.

Additionally or alternatively a sixth non-limiting example takes the form of a method as in any one of the first to fourth non-limiting examples, wherein the lead is a bifurcated lead with first and second electrodes disposed on first and second lead branches.

Additionally or alternatively a seventh non-limiting example takes the form of a method as in the sixth non-limiting example, wherein the step of advancing the distal end of the lead through the sheath and into the ITV comprises advancing a distal end of the first lead branch in a superior direction and advancing a distal end of the second lead branch in an inferior direction.

Additionally or alternatively an eighth non-limiting example takes the form of a method as in any one of the second to seventh non-limiting examples, wherein the intercostal space is between ribs 2 and 3 or between ribs 3 and 4.

Additionally or alternatively an ninth non-limiting example takes the form of a method as in any one of the second to seventh non-limiting examples, wherein the intercostal space is between ribs 4 and 5 or between ribs 5 and 6.

Additionally or alternatively a tenth non-limiting example takes the form of a method as in any one of the second to ninth non-limiting examples, further comprising tunneling from the left axilla to the intercostal space, attaching an implantable pulse generator to the lead and implanting the pulse generator at the left axilla.

Additionally or alternatively a eleventh non-limiting example takes the form of a method as in any one of the first to tenth non-limiting examples, further comprising anchoring the lead in the ITV using an inflatable balloon.

Additionally or alternatively an twelfth non-limiting example takes the form of a method as in any one of the first to tenth non-limiting examples, further comprising anchoring the lead in the ITV using an expandable member, the expandable member selected from the group consisting of a lobe, a tine, a hook, or a stent.

Additionally or alternatively a thirteenth non-limiting example takes the form of a method as in any one of the first to twelfth non-limiting examples, wherein the lead is configured to have a curvature and the method further comprises anchoring the lead by allowing it to assume the curvature once inserted into the ITV.

Additionally or alternatively a fourteenth non-limiting example takes the form of a method as in any one of the first to thirteenth non-limiting examples, further comprising attaching a suture sleeve and suturing the suture sleeve to subcutaneous tissue and to the lead to hold the lead in position.

Additionally or alternatively a fifteenth non-limiting example takes the form of a method as in any one of the first to fourteenth non-limiting examples, wherein the ITV is the right ITV.

Additionally or alternatively a sixteenth non-limiting example takes the form of a method as in any one of the first to fourteenth non-limiting examples, wherein the ITV is the left ITV.

Additionally or alternatively a seventeenth non-limiting example takes the form of a method of implanting a cardiac stimulus system parasternally in a patient, the method comprising performing the method of any one of the first to fourteenth non-limiting examples to implant a first lead in the right ITV, performing the method of any one of the first to fourteenth non-limiting examples to implant a second lead in the left ITV, and coupling the first and second leads to a pulse generator for the cardiac stimulus system.

A eighteenth non-limiting example takes the form of a method of treating a patient comprising delivering therapy between a first electrode disposed on a lead which is placed parasternally in an ITV and at least a second electrode.

Additionally or alternatively an nineteenth non-limiting example takes the form of a method as in the eighteenth non-limiting example, wherein the therapy is a defibrillation therapy, and the second electrode is disposed on an implantable pulse generator also placed in the patient.

Additionally or alternatively a twentieth non-limiting example takes the form of a method as in the nineteenth non-limiting example, wherein the implantable pulse generator is in the left axilla, and the lead and electrode are in the right ITV.

Additionally or alternatively a twenty-first non-limiting example takes the form of a method as in the nineteenth non-limiting example, wherein the implantable pulse generator is in the left axilla, and the lead and electrode are in the left ITV.

Additionally or alternatively a twenty-second non-limiting example takes the form of a method as in the nineteenth non-limiting example, wherein the implantable pulse generator is placed in a subclavicular pectoral position on the patient's chest.

Additionally or alternatively a twenty-third non-limiting example takes the form of a method as in the eighteenth non-limiting example, wherein the therapy is a bradycardia pacing therapy.

Additionally or alternatively a twenty-fourth non-limiting example takes the form of a method as in the eighteenth non-limiting example, wherein the therapy is an anti-tachycardia pacing therapy.

Additionally or alternatively a twenty-fifth non-limiting example takes the form of a method as in the eighteenth non-limiting example, wherein the therapy is a cardiac resynchronization therapy.

Additionally or alternatively a twenty-sixth non-limiting example takes the form of a method as in any one of the twenty-third to twenty-fifth non-limiting examples, wherein the second electrode is also disposed in an ITV.

Additionally or alternatively a twenty-seventh non-limiting example takes the form of a method as in the twenty-sixth non-limiting example, wherein both the first and second electrodes are disposed on a single lead in the right ITV.

Additionally or alternatively a twenty-eighth non-limiting example takes the form of a method as in the twenty-sixth non-limiting example, wherein both the first and second electrodes are disposed on a single lead in the left ITV.

Additionally or alternatively a twenty-ninth non-limiting example takes the form of a method as in the twenty-sixth non-limiting example, wherein the first electrode is in the right ITV, and the second electrode is in the left ITV.

Additionally or alternatively a thirtieth non-limiting example takes the form of a method as in any one of the twenty-third to twenty-fifth non-limiting examples, wherein the second electrode is disposed on an implantable pulse generator also implanted in the patient.

Additionally or alternatively a thirty-first non-limiting example takes the form of a method as in the thirtieth non-limiting example, wherein the implantable pulse generator is in the left axilla, and the lead and electrode are in the right ITV.

Additionally or alternatively a thirty-second non-limiting example takes the form of a method as in the thirtieth non-limiting example, wherein the implantable pulse generator is in the left axilla, and the lead and electrode are in the left ITV.

Additionally or alternatively a thirty-first non-limiting example takes the form of a method as in the thirtieth non-limiting example, wherein the implantable pulse generator is placed in a subclavicular pectoral position on the patient's chest.

Additionally or alternatively a thirty-fourth non-limiting example takes the form of a method as in the eighteenth non-limiting example, wherein the therapy is a defibrillation therapy and both the first and second electrodes are disposed on a single lead within the same ITV.

Additionally or alternatively a thirty-fifth non-limiting example takes the form of a method as in the eighteenth non-limiting example, wherein the therapy is a defibrillation therapy and the second electrode is disposed subcutaneously on a lead in the patient.

Additionally or alternatively a thirty-sixth non-limiting example takes the form of a method as in the eighteenth non-limiting example, wherein the therapy is a defibrillation therapy, wherein the first electrode is electrically in common with a third electrode during the therapy delivery.

Additionally or alternatively a thirty-seventh non-limiting example takes the form of a method as in the thirty-sixth non-limiting example, wherein the third electrode is disposed in the same ITV as the first electrode.

Additionally or alternatively a thirty-eighth non-limiting example takes the form of a method as in the thirty-sixth non-limiting example, wherein the third electrode is disposed in an ITV such that one of the first and third electrodes is in the right ITV, and the other of the first and third electrodes is in the left ITV.

Additionally or alternatively a thirty-ninth non-limiting example takes the form of a method as in any one of the eighteenth to thirty-seventh non-limiting examples, wherein the first electrode is a composite electrode including at least a first coil electrode electrically in common with a first ring electrode.

Additionally or alternatively a fortieth non-limiting example takes the form of a method as in any one of the eighteenth to thirty-eighth non-limiting examples, wherein the first electrode is a composite electrode including at least first and second coil electrodes electrically in common with one another.

A forty-first non-limiting examples takes the form of a method of implanting a lead parasternally for use in a cardiac stimulus system in a patient, the lead having at least one electrode thereon; the method comprising establishing access to an ITV through an intercostal space between two ribs, inserting a distal end of a lead into the ITV, advancing the lead to a desired location parasternally relative to the heart of a patient, and securing the lead in place.

Additionally or alternatively a forty-second non-limiting example takes the form of an implantation tool set configured for use in a method as in any one of first to seventeenth non-limiting examples. Such a tool set may comprise an ultrasound needle, a guidewire sized and adapted to pass through a lumen in the ultrasound needle, and a sheath adapted for place over the guidewire.

Additionally or alternatively, a forty-third non-limiting example may take the form of an implantable cardiac stimulus device comprising a lead and an implantable canister for coupling to the lead, the implantable canister housing operational circuitry configured to deliver output therapy in the form of at least one of bradycardia pacing, anti-tachycardia pacing, cardiac resynchronization therapy, or defibrillation, according to a method as in any of the eighteenth to forty-first non-limiting examples.

A forty-fourth non-limiting example takes the form of an implantable cardiac stimulus device for implantation in the internal thoracic vein (ITV) comprising an implantable canister housing operational circuitry configured to delivery output therapy in the form of at least one of bradycardia pacing, anti-tachycardia pacing, cardiac resynchronization therapy, or defibrillation, and a bifurcated lead having a proximal end coupled to the implantable canister, and at least first and second fingers extending from a bifurcation element at a distal end of the lead, wherein each of the first and second fingers has one or more electrode disposed thereon, wherein the first and second fingers are configured to extend in opposite directions distal of the connection element.

Additionally or alternatively, a forty-fifth non-limiting example may take the form of the implantable cardiac stimulus device of the forty-fourth non-limiting example, wherein each of the first and second fingers includes a terminal electrode and a coil electrode.

Additionally or alternatively, a forty-sixth non-limiting example may take the form of the implantable cardiac stimulus device of the forty-fourth or forty-fifth non-limiting example, wherein one of the first and second fingers includes a second electrode.

Additionally or alternatively, a forty-seventh non-limiting example may take the form of the implantable cardiac stimulus device of any of the forty-fourth to forty-sixth non-limiting examples, wherein at least one of the first and second fingers has a shocking electrode disposed thereon and at least one of the first and second fingers has one or more sensing or pacing electrode disposed thereon.

Additionally or alternatively, a forty-eighth non-limiting example may take the form of the implantable cardiac stimulus device of any of the forty-fourth to forty-seventh non-limiting examples, wherein the first finger includes a sensing or pacing electrode and a shocking coil electrode and the second finger includes first and second sensing or pacing electrodes and a shocking coil electrode.

Additionally or alternatively, a forty-ninth non-limiting example may take the form of the implantable cardiac stimulus device of any of the forty-fourth to forty-seventh non-limiting examples, wherein the first and second fingers each includes at least two sensing or pacing electrodes.

Additionally or alternatively, a fiftieth non-limiting example may take the form of the implantable cardiac stimulus device of any of the forty-fourth to forty-seventh non-limiting examples, wherein the first finger includes a shocking coil electrode and the second finger includes at least two sensing or pacing electrodes.

Additionally or alternatively, a fifty-first non-limiting example may take the form of the implantable cardiac stimulus device of any of the forty-fourth to forty-seventh non-limiting examples, wherein each of the first and second fingers includes a shocking coil electrode disposed between first and second sending or pacing electrodes.

Additionally or alternatively, a fifty-second non-limiting example may take the form of the implantable cardiac stimulus device of any of the forty-fourth to fifty-first non-limiting examples, wherein the bifurcation element includes one or more attachment structure.

Additionally or alternatively, a fifty-third non-limiting example may take the form of the implantable cardiac stimulus device of the fifty-second non-limiting example, wherein the attachment structure includes one or more suture loops.

Additionally or alternatively, a fifty-fourth non-limiting example may take the form of the implantable cardiac stimulus device of the fifty-second non-limiting example, wherein the attachment structure includes a suture sleeve with one or more grooves disposed therein.

A fifty-fifth non-limiting example may take the form of an implantable cardiac stimulus device comprising an implantable canister housing operational circuitry configured to delivery output therapy in the form of at least one of bradycardia pacing, anti-tachycardia pacing, cardiac resynchronization therapy, or defibrillation, and first and second leads each having a proximal end coupled to the implantable canister and a distal end, the first and second leads each having one or more electrodes disposed adjacent the distal end, wherein the first and second leads are connected at a connection element disposed proximal of the one or more electrodes, wherein the first and second leads are configured to extend in opposite directions distal of the connection element.

Additionally or alternatively, a fifty-sixth non-limiting example may take the form of the implantable cardiac stimulus device of the fifty-fifth non-limiting example, wherein each of the first and second leads includes a terminal electrode and a coil electrode.

Additionally or alternatively, a fifty-seventh non-limiting example may take the form of the implantable cardiac stimulus device of the fifty-fifth or fifty-sixth non-limiting example, wherein one of the first and second leads includes a second electrode.

Additionally or alternatively, a fifty-eighth non-limiting example may take the form of the implantable cardiac stimulus device of any of the fifty-fifth to fifty-seventh non-limiting examples, wherein at least one of the first and second leads has a shocking electrode disposed thereon and at least one of the first and second leads has one or more sensing or pacing electrode disposed thereon.

Additionally or alternatively, a fifty-ninth non-limiting example may take the form of the implantable cardiac stimulus device of any of the fifty-fifth to fifty-seventh non-limiting examples, wherein the first lead includes a sensing or pacing electrode and a shocking coil electrode and the second lead includes first and second sensing or pacing electrodes and a shocking coil electrode.

Additionally or alternatively, a sixtieth non-limiting example may take the form of the implantable cardiac stimulus device of any of the fifty-fifth to fifty-seventh non-limiting examples, wherein the first and second leads each includes at least two sensing or pacing electrodes.

Additionally or alternatively, a sixty-first non-limiting example may take the form of the implantable cardiac stimulus device of any of the fifty-fifth to fifty-seventh non-limiting examples, wherein the first lead includes a shocking coil electrode and the second lead includes at least two sensing or pacing electrodes.

Additionally or alternatively, a sixty-second non-limiting example may take the form of the implantable cardiac stimulus device of any of the fifty-fifth to fifty-seventh non-limiting examples, wherein each of the first and second leads includes a shocking coil electrode disposed between first and second sending or pacing electrodes.

Additionally or alternatively, a sixty-third non-limiting example may take the form of the implantable cardiac stimulus device of any of the fifty-fifth to sixty-second non-limiting examples, wherein the connection element includes one or more attachment structure.

Additionally or alternatively, a sixty-fourth non-limiting example may take the form of the implantable cardiac stimulus device of the sixty-third non-limiting example, wherein the attachment structure includes one or more suture loops.

Additionally or alternatively, a sixty-fifth non-limiting example may take the form of the implantable cardiac stimulus device of the sixty-first non-limiting example, wherein the attachment structure includes a suture sleeve with one or more grooves disposed therein.

Each of these non-limiting examples can stand on its own, or can be combined in various permutations or combinations with one or more of the other examples. This overview is intended to provide an introduction to the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 3A and 3B show the ITVs and linked vasculature in isolation;

FIGS. 6A-6C show superior access and parasternal implantation in the left ITV;

DETAILED DESCRIPTION

Figure 1:
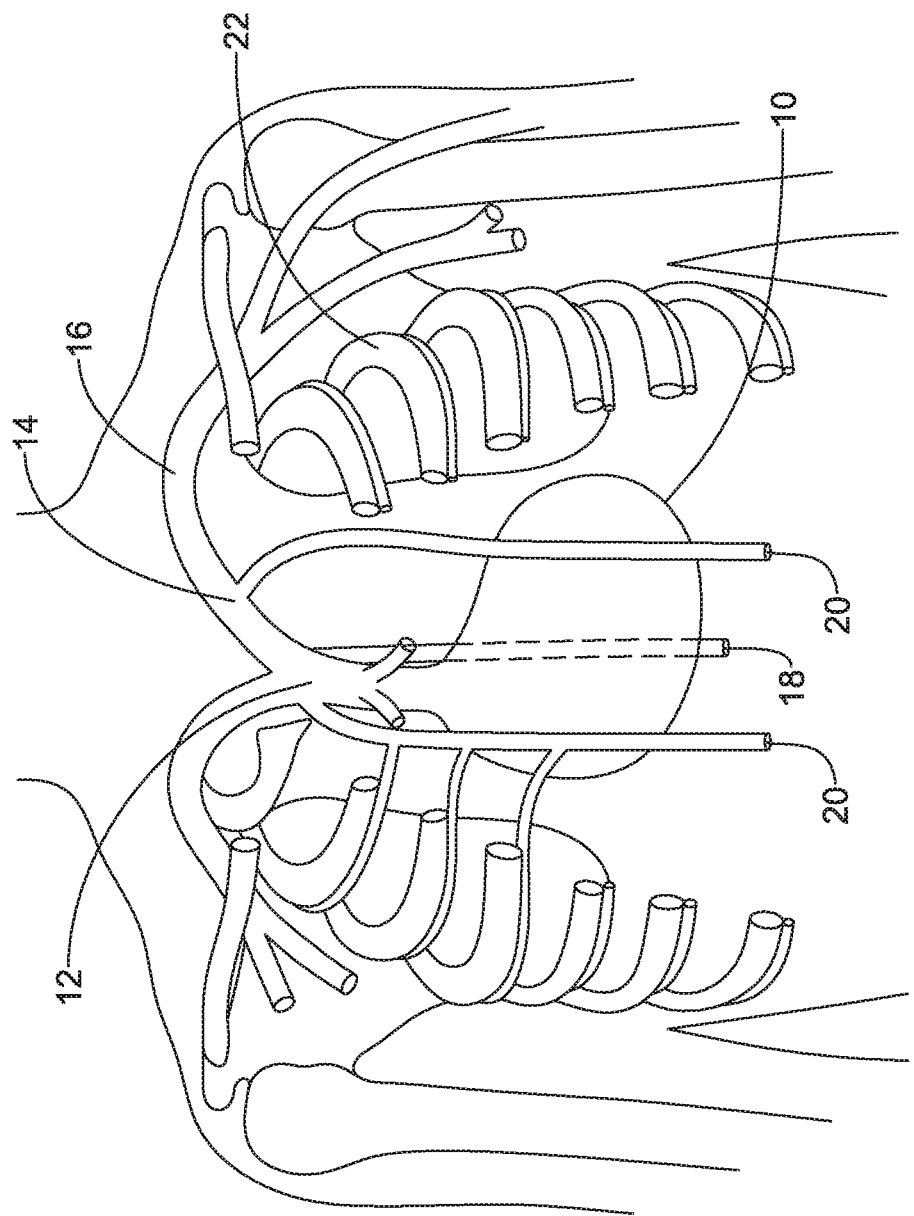
FIG. 1 illustrates the thoracic anatomy including placement of the internal thoracic veins (ITVs)

The S-ICD System from Boston Scientific provides benefits to the patient including the preservation of transvenous anatomy and avoidance of intracardiac leads, which may fracture and/or may serve as conduits for infection to reach the heart, and can occlude blood vessels going into the heart, making later placement of leads or other devices in the heart more difficult. Some examples and discussion of subcutaneous lead implantation may be found in U.S. Pat. No. 8,157,813, titled APPARATUS AND METHOD FOR SUBCUTANEOUS ELECTRODE INSERTION, and US PG Publication No. 20120029335, titled SUBCUTANEOUS LEADS AND METHODS OF IMPLANT AND EXPLANT, the disclosures of which are incorporated herein by reference. Additional subcutaneous placements are discussed in U.S. Pat. No. 6,721,597, titled SUBCUTANEOUS ONLY IMPLANTABLE CARDIOVERTER DEFIBRILLATOR AND OPTIONAL PACER, and the above mentioned U.S. Pat. No. 7,149,575, the disclosures of which are incorporated herein by reference.

While many patients can be well treated with the S-ICD System, there continue to be limitations. Increased energy requirements of the S-ICD System, perceived difficulty with providing chronic bradycardia pacing, and unavailability of anti-tachycardia pacing to terminate select fast tachycardia, have created interest in alternative defibrillator and/or pacemaker placement techniques. One proposal has included a substernal placement, with a lead extending beneath the sternum from a position inferior to the lower rib margin, such as in US PG Patent Application Pub. No. 20170021159, titled SUBSTERNAL PLACEMENT OF A PACING OR DEFIBRILLATING ELECTRODE, the disclosure of which is incorporated herein by reference. Proposals for a substernal device have been referred to as extravascular, insofar as the lead does not enter or reside in the vasculature. Such devices are distinct from early generation epicardial devices in that the lead and electrode would not touch the heart or enter or be secured to the pericardium.

A further alternative placement involves inserting a lead into the internal thoracic vein (ITV), also referred to as the internal mammary vein, from a superior or inferior approach, such as in U.S. patent application Ser. No. 15/667,167, titled IMPLANTATION OF AN ACTIVE MEDICAL DEVICE USING THE INTERNAL THORACIC VASCULATURE, the disclosure of which is incorporated herein by reference.

The internal thoracic vein (ITV) is a vessel that drains the chest wall and breasts. There are both left and right internal thoracic veins on either side of the sternum, beneath the ribs. The ITV arises from the superior epigastric vein, accompanies the internal thoracic artery along its course and terminates in the brachiocephalic vein. The inventor has recognized that the ITV may make a suitable location for placement of a cardiac stimulus lead, and the ITV may be accessed parasternally, for example through one of the intercostal spaces. The parasternal method of accessing the ITV may allow for more predictable access than a superior or inferior approach, given the increase in diameter of the vein as it rises superiorly in the thorax. Further, the ITVs are consistently located approximately 1 cm from the sternum.

While variability may still occur, the parasternal approach may allow for blind or guided percutaneous access to the ITV. While much of the following disclosure focuses on the use of the ITV, many of these concepts could also be applied to the internal thoracic arteries, which may sometimes be referenced as the internal mammary arteries.

Figure 4:
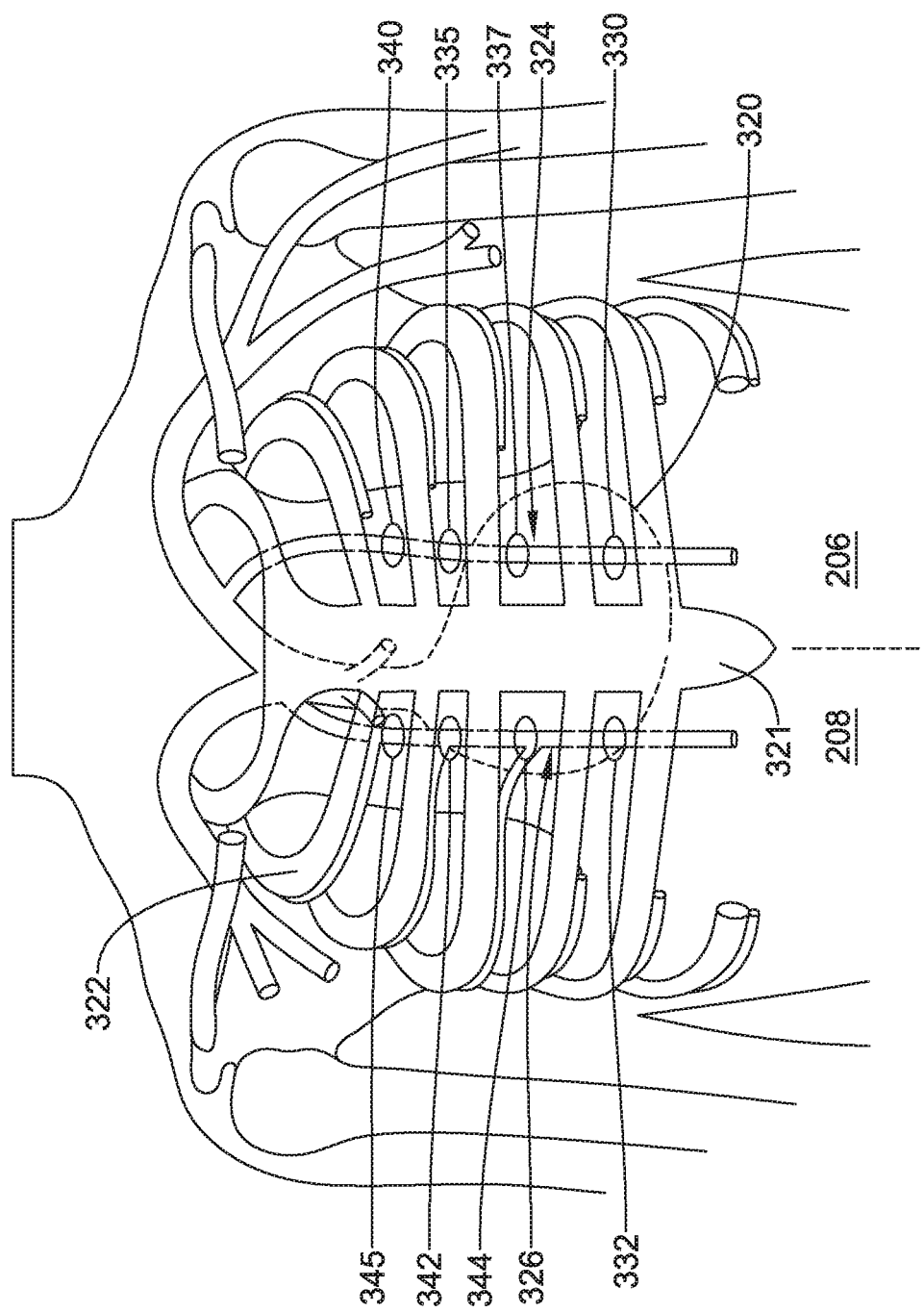
FIG. 4 illustrates access locations usable for parasternal access to the ITVs.

FIG. 1 illustrates portions of the thoracic anatomy including location of the internal thoracic veins (ITVs). The ribcage is shown at 22 and an outline of the heart is shown at 10, with the superior vena cava (SVC) shown at 12. The brachiocephalic veins 14 couple to the SVC and extend past various cephalic branches to the subclavian vein 16. The azygos vein is shown at 18 and the right and left ITVs are shown at 20. The sternum is not shown to allow visualization of the heart in relation to the ITVs. FIG. 4 shows the position of the ITVs in relation to the sternum.

Certain literature in the field of implantable pacemakers or defibrillators has noted the possibility of the using the azygos vein to implant a lead and electrode to stimulate the vagus nerve (see, for example, U.S. Pat. No. 8,005,543, the disclosure of which is incorporated herein by reference), or as an adjunct to defibrillator function (see Cesario et al., "Azygos vein lead implantation: a novel adjunctive technique for implantable cardioverter defibrillator placement," J. Cardiovasc. Electrophysiol., 2004, 15:780-783). However, such proposals have not found widespread acceptance. It does not appear that the ITVs 20 have been proposed, and in particular, parasternal access to the ITVs nowhere appears to be discussed.

Figure 2:
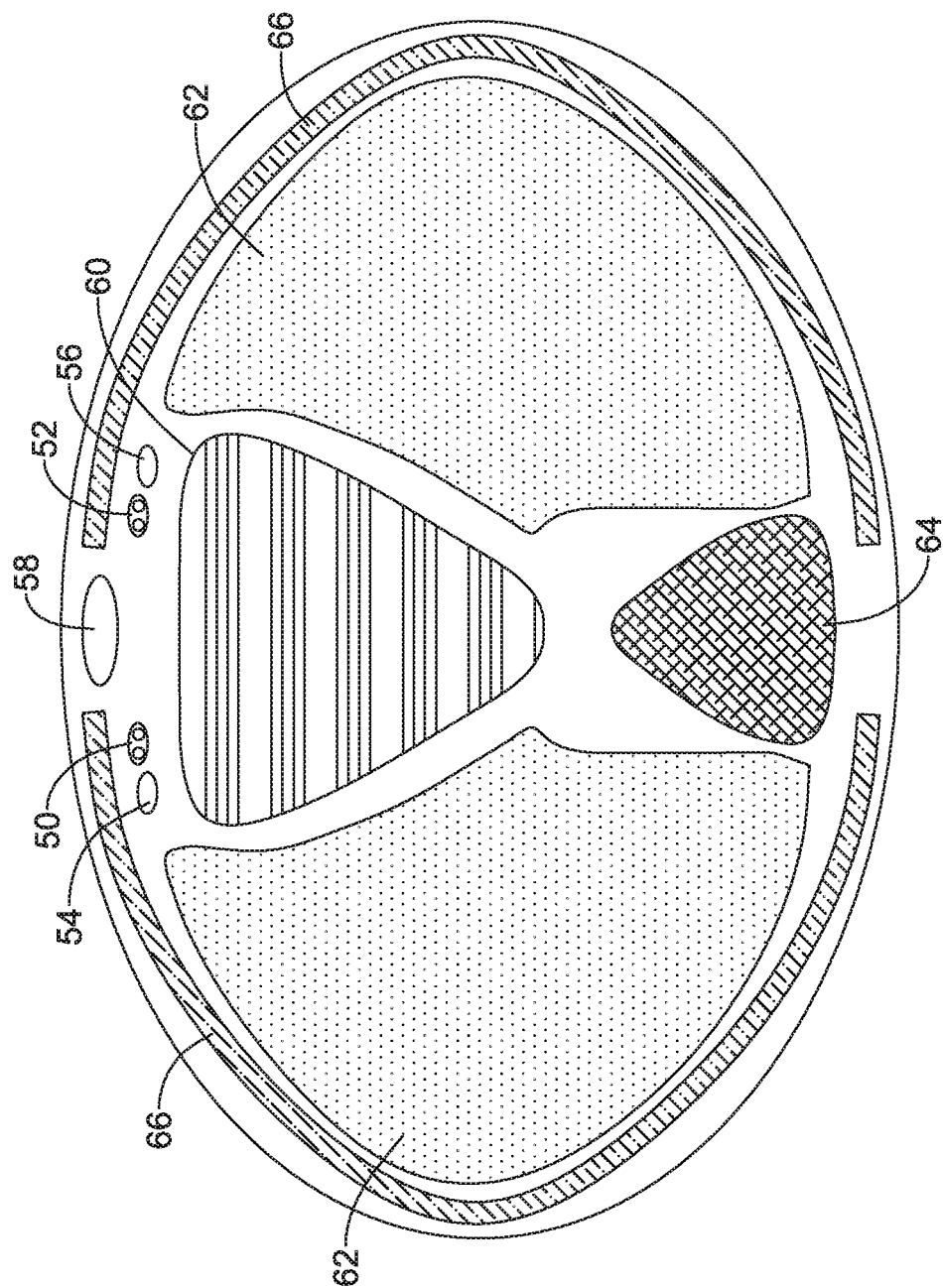
FIG. 2 shows the torso in a section view to highlight the location of the ITVs and arteries.

FIG. 2 shows the torso in a section view to highlight the location of the ITVs and internal thoracic arteries. More particularly, in the example, the right and left ITV are shown at 50, 52, running parallel to and more central of the internal thoracic arteries 54, 56, on either side of the sternum 58. The heart is shown at 60, with the lungs at 62 and spinal column at 64. The ITV 50, 52 lie beneath the ribs 66 but outside and separate from the pleurae of lungs 62. As used herein, the "ITV" is the name applied for the vein while it runs beneath the chest, that is, superior to the lower margin of the ribs. Inferior to the lower margin of the ribs, the blood vessel continues as the superior epigastric vein. The relatively superficial position makes the ITV 50, 52 accessible percutaneously through intercostal spaces between ribs 66 as further discussed below. Parasternal access to the ITV may be made from an access point between the ribs, which may be referred to as intercostal space. However, in the discussion below, the term parasternal is used as it more specifically describes accessing the ITV at a location adjacent the sternum, and includes accessing the ITV at any location along the length of the ITV, adjacent the sternum.

FIGS. 3A-3B show the ITV and linked vasculature in isolation. FIG. 3A is an anterior view of selected portions of the venous structure of the upper torso, and FIG. 3B is a lateral view of the same. The SVC is shown at 100, with the brachiocephalic veins 102 splitting at the upper end of the SVC. The right subclavian vein is at 104, and the left subclavian vein is at 106. The azygos vein is include in the illustration at 108, extending off the posterior of the SVC, and runs inferiorly posterior of the heart as can be understood from the lateral view of FIG. 3B. The right and left ITV are shown at 110, 112. These each branch off at a location that is considered part of the brachiocephalic veins 102. The internal jugular veins are also shown at 114.

FIG. 4 shows various parasternal access points for implantation of a lead in the ITV. The heart is shown at 320 beneath the ribcage 322 and sternum 321, with the right ITV at 326 on the right side of the body 208 and the left ITV at 324 on the left side of the body 206. Parasternal access to the ITVs may be achieved at any location, however, more superior or inferior positions may be preferred to allow passage of the distal end of a lead along a significant region of the ventricles and atria by passing in a particular direction. Access locations into the left ITV 324 are shown at 330, 335, 337, and 340 and access locations into the right ITV 326 are shown at 332, 344, 342, and 345. The ITV may be accessed using standard access techniques known in the art for implanting traditional transvenous pacemakers and defibrillators.

In the example shown in FIG. 4, illustrative access locations for parasternal lead implantation are shown at relatively inferior positions such as access locations 330 and 332, between ribs 5 and 6, and access locations 337 and 344, between ribs 4 and 5. More superior positions include access locations 335 and 342, between ribs 3 and 4, and access locations 340 and 345, between ribs 2 and 3. In any location, access may be achieved using ultrasound guided needle insertion. The access method may resemble the Seldinger technique, though in this case the muscle adjacent the sternum in the intercostal space would first be traversed. Other venipuncture or cutdown techniques may be used instead.

The Seldinger technique may include creating a puncture at one of the access locations 330, 335, 335, 340, 332, 344, 342, or 345, with a hollow needle or trocar, for example under ultrasound guidance, introducing a guidewire through the needle and into the desired blood vessel, removing the needle, keeping the guidewire in place, and then inserting an introducer sheath, which may have a valve at its proximal end, over the guidewire.

The introducer sheath may be advanced to a location to place its distal tip near the desired location of the distal end of the lead. Contrast injection may be useful to visualize the ITV structures. A guide catheter and guidewire may then be introduced through the introducer sheath. The guidewire may be the same as used in gaining initial access (if one is used to gain access), or may be a different guidewire.

In another example, a cut-down technique may be used to access the desired ITV 326, 324 by incision through the skin. The incision may be made laterally from the location of the ITV. Next, possibly after visual confirmation the desired vessel is accessed, incision into the selected vein can be made, followed by direct insertion of the lead into the ITV. The limited angulation involved with inserting the lead into the ITV from a parasternal access point may allow the lead to be inserted directly into the ITV, without the use of a guidewire or sheath. This may provide a faster and simpler lead placement method. Alternatively, the above described insertion of a guidewire and introducer sheath may be used for placement of the lead into the ITV.

In animal testing the present inventors have determined that access to the ITV can be achieved parasternally with little difficulty to facilitate lead placement by accessing the ITV between various ribs. It is recognized that the human anatomy will be different from that of the tested animal (porcine model), and may further vary with the particular body characteristics of a given patient including, for example, any venous abnormality, scarring in the area (such as related to any prior sternotomy or the like) as well as the body habitus (overweight or underweight patients). However, the sternum is readily accessible as relatively little tissue (including muscle and fat) is disposed over the sternum regardless of body composition.

Figure 5:
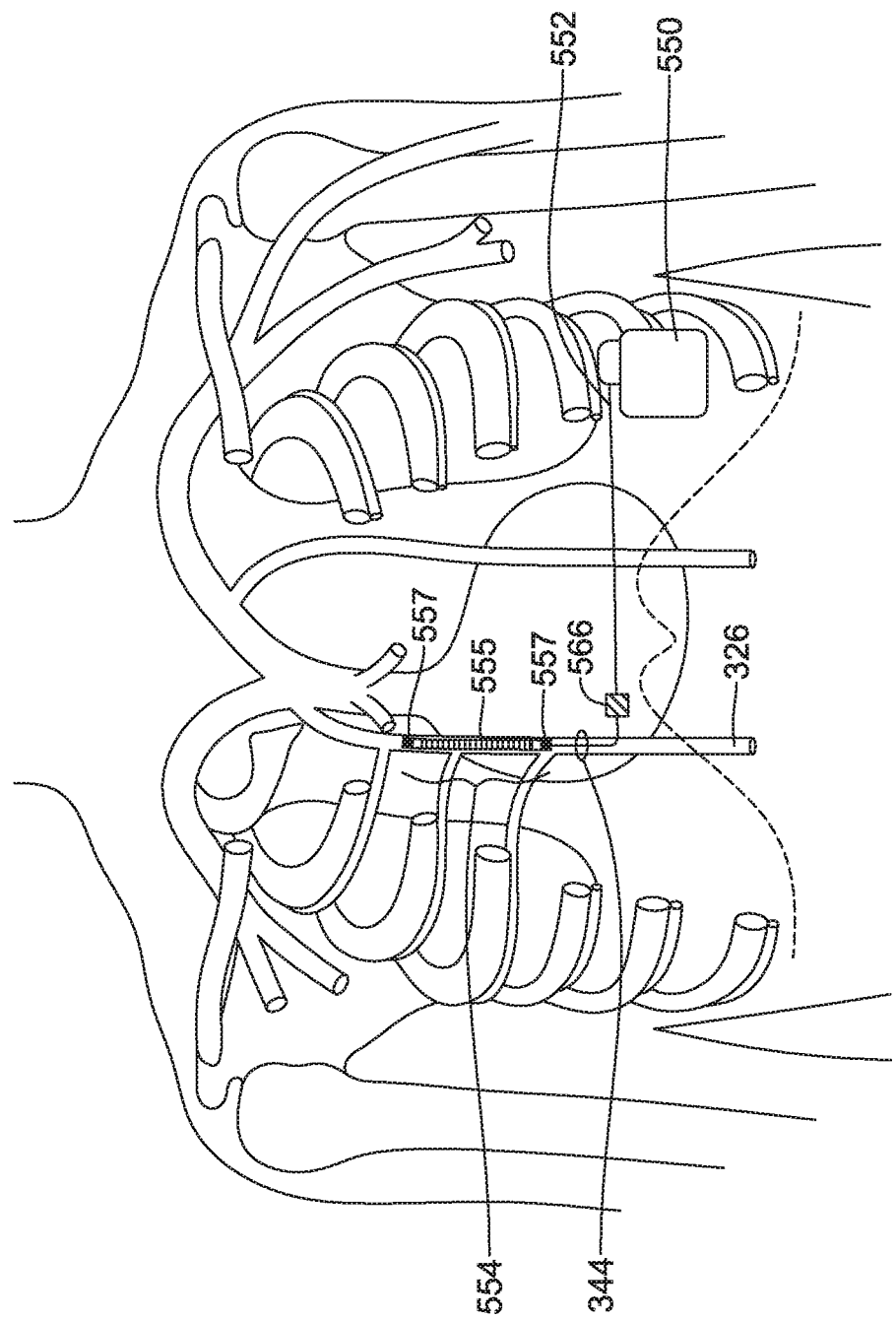
FIG. 5 shows inferior access and parasternal implantation in the right ITV.

Once access to a selected ITV 326, 324 is achieved, the vessel can be traversed in a superior or inferior direction to place the lead at a desired level by entering the corresponding ITV. FIG. 5 shows parasternal implantation using an inferior access position into the right ITV 326 with implantation of an electrode structure 554 extending in a superior direction. In this example, an implantable system having an implantable pulse generator 550 and lead 552 with distal electrode structure 554 has been emplaced in a patient. The right ITV 326 is accessed using access location 344. As shown, the electrode structure 554 includes a coil electrode 555 flanked with two sensing electrodes 557; other combinations of electrodes may be used. The distal portion of the electrode structure 554 may include a fixation apparatus or shape for the flexible lead, such as a 2 or 3 dimensional curve (see FIGS. 12-13), tines (see FIG. 14), an expandable member (see FIG. 17), or hooks or a side-extending engagement structure (see FIG. 18) as described below.

The access at access location 344 may be achieved percutaneously by inserting a needle, preferably under guidance such as by the use of an ultrasound guided needle, into the chosen intercostal space at location 344, for example, low on the ribcage and near the sternum, through the muscle of the intercostal space and into the right ITV 326. A guidewire can be passed through the needle and an introducer sheath passed over the guidewire after removal of the needle. Other techniques may be used instead, and other access points may be selected, such as those shown in FIG. 4 and discussed above.

A suture sleeve 566 may be used to secure the lead 552 over the ribcage as desired. The lead 552, as with all other implanted leads shown herein, may include a fixation structure such as bends or curves along its distal length, or tines, hooks or expandable members at its distal end to secure its position within the ITV 326.

Figure 6A:
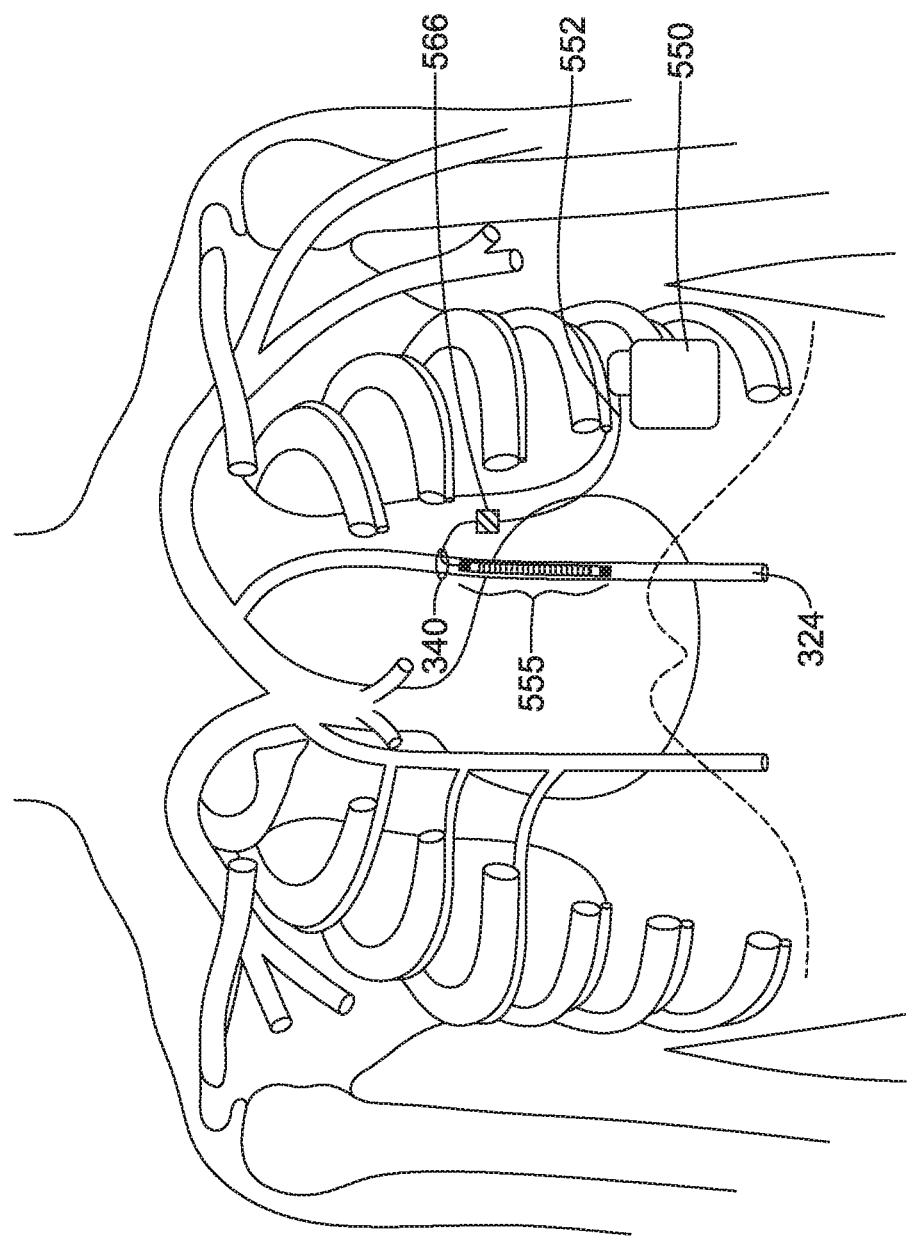

FIG. 6A shows parasternal implantation using a superior access location 340 into the left ITV 324 with implantation of an electrode structure 555 extending in an inferior direction. As in the example shown in FIG. 5, this method involves implantation of an implantable pulse generator 550 and lead 552. The lead 552 is tunneled from the parasternal access location 340 down to the pulse generator 550, which may be implanted at the left axilla as illustrated, and a suture sleeve 566 may be used to secure the lead 552 over the ribcage. The pulse generator 550 may instead be implanted in a generally subclavicular location, if desired.

In some examples, a flexible lead may be introduced with the support of a guide catheter during advancement. The guide catheter may receive the lead through a guide catheter lumen that serves to retain a fixation apparatus or shape for the flexible lead, such as a 2-dimensional or 3-dimensional curvature (see FIGS. 12-13), tines (see FIG. 14), an expandable member (see FIG. 17), or hooks or a side-extending engagement structure (see FIG. 18). A stylet may be placed through the lead, or a portion thereof, to retain a straight shape during implantation; upon removal of the stylet, a curvature (see FIGS. 12-13) may then be released for securing the lead in place.

In another alternative, the guide catheter and guidewire may be omitted by providing a lead with a flexible or steerable structure, and/or a lead configured for implantation using a steerable stylet. For example, a lead may be configured to be implanted using a steerable stylet in a lumen thereof, with the initial placement into the left ITV 324 (or right ITV 326, if desired) at the distal end of the introducer sheath, possibly using contrast visualization, if desired. Once initial access is achieved, simply pushing the stylet should be sufficient to implant the lead to a desired level in the ITV. The stylet may have a secondary function of preventing an anchoring structure of the lead from assuming an anchoring shape or releasing an anchoring tine, hook, expandable member, stent or other device.

Figure 6B:
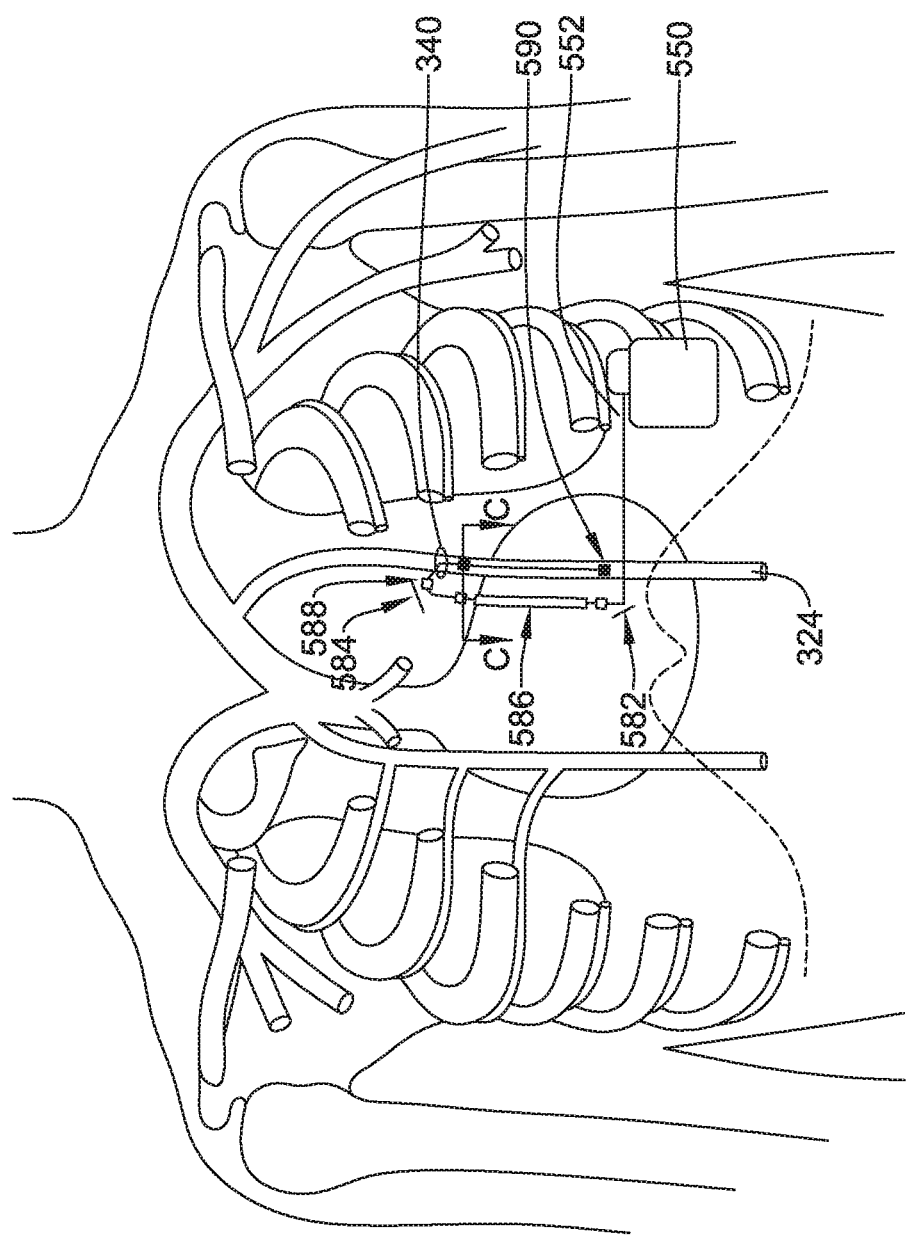

FIG. 6A illustrates a method where tunneling may traverse the inframammary crease to the point where the ITV is accessed at 340. In another example, a traditional S-ICD System implant pathway is used, as shown in FIG. 6B. In this example, an implantable pulse generator 550 is shown generally at the left axilla, with a lead 552 extending medially therefrom toward the xiphoid. A xiphoid incision is shown at 582 for illustrative purposes. From the xiphoid incision 582 the lead 552 extends superiorly along and just left of the sternum (not shown) to an upper sternal incision shown at 584. Near the upper sternal incision, the lead 580 is shown extending through an ITV access at 340 into the left ITV 324. From access point 340, the lead extends inferiorly within the ITV.

In the illustrative example, the lead 552 is shown including an electrode assembly at 586, with proximal and distal sense electrodes around a shocking coil electrode, as is known for the S-ICD System (fewer or more electrodes, or a different arrangement, may be provided). However, the distal portion of the lead 552 extends beyond the superior sensing electrode to enter the ITV. In the example, a suture sleeve or other fixation member may be provided at 588 to prevent movement of the lead 552 once implantation is completed. In this example, the suture sleeve 588 secures a first portion of the lead 552 relative to the ITV and a second portion of the lead 552 relative to a parasternal subcutaneous tunnel in which the subcutaneous electrode assembly 586 is placed.

Within the ITV 324, the lead 552 is shown with pace/sense electrodes at 590. In the example, the lead 552 may taper from a greater diameter in the portion that resides subcutaneously to a lesser diameter for entry into the ITV. For example, the lead 552 may taper from a size in the range of 8 to 12 French, down to a size of 4 to 7 French, or even down to a size of 2 French, as desired, such that the more distal portion can enter the ITV more readily than the larger more proximal portion. In still another alterative example, the lead may be cylindrical and lacking a tapered or narrowed region.

In an example, subcutaneous implantation may be performed using a proximal end pulling technique, wherein the lead is implanted by pulling the proximal end thereof from the upper sternal incision 584 to the xiphoid incision 582, and then from the xiphoid incision 582 to the axillary pocket for the canister, thus protecting the smaller distal portion thereof from the forces associated with implantation and from environmental exposure to microbes. In an example, the ITV implantation may occur last, after the subcutaneous portion is placed, with the suture sleeve 588 applied after the ITV placement is completed. The suture sleeve 588 may include a portion adapted to place adjacent the ITV access to partly close the access location. The suture sleeve 588 may include a coating thereon for anti-microbial purposes to prevent or slow the advancement of any subcutaneous infection into the vein, should such an infection occur.

In an example, the system as in FIG. 6B may deliver defibrillation therapy using a subcutaneously placed coil electrode such as a coil electrode that is part of the subcutaneous lead assembly 586, as one of the anode or cathode for defibrillation therapy, in opposition to the housing of the implantable pulse generator 550. Meanwhile, pacing may be performed using the electrodes 590 placed in the ITV as anode/cathode, or using one of the electrodes 590 in the ITV paired with the pulse generator 550. In a further example, one electrode in the ITV may be used for bradycardia pacing (the superior electrode, which may be level with the AV junction), while the other electrode (the inferior electrode, which may be level with the ventricles) is used for anti-tachycardia pacing (ATP), each using the implantable pulse generator 550 as opposing electrode. In still another example, a pacing stimulus may be applied using the two ITV electrodes 590 for bradycardia, and using only the inferior of the ITV electrodes paired with the implantable pulse generator 550 for ATP pacing. Sensing on the other hand may be performed using any suitable pairing of electrodes; a likely combination is believed to be the use of the subcutaneous electrodes for sensing generally, with one of the ITV electrodes used in monopolar sensing configuration, or the pair of ITV electrodes in a bipolar sensing configuration, as an occasional backup for rate sensing purposes. In these examples, bradycardia pacing may include post-shock bradycardia pacing following defibrillation stimulus delivery. For example, the ITV electrodes 590 may be used to deliver post-shock bradycardia pacing after delivery of defibrillation therapy using the subcutaneous electrode assembly and the pulse generator housing.

In another example, electrode switching may be performed following delivery of a defibrillation shock to avoid post-shock defibrillation. As outlined in U.S. Pat. No. 8,483,841, localized polarization of the sensing electrodes and/or canister following delivery of a defibrillation stimulus can hamper sensing.

In an example, the subcutaneous electrode assembly 586 may be used to deliver defibrillation therapy, and, following such therapy, the system sensing configuration may be switched to use the ITV electrodes for example, for a minimum period of time or until some detected condition suggests that the pre-shock sensing configuration is clear of any post-shock polarization. Thus, for example, the implantable pulse generator would house operational circuitry including sensing circuitry adapted use a sensing configuration to select electrodes to provide sensing inputs used to detect cardiac conditions of the patient, and an illustrative method would comprising modifying a sensing configuration of the sensing circuitry to use electrodes on the second portion of the lead following the defibrillation therapy. In another example, the operational circuitry may be configured to automatically implement a post-shock sensing mode using the ITV electrodes in place of another default electrode configuration.

FIG. 6C is a partial section view as indicated at C-C in FIG. 6B. Here, it can be seen that the subcutaneous electrode assembly 586 sits between the ribs and the skin. Depending on implant technique, the subcutaneous electrode assembly 586 and lead 552 may be implanted in the range of about 2 centimeters left of midline to about 2 centimeters left of the sternal margin (other locations may be used, if desired). The pacing electrode 590 is shown within the ITV 324, beneath the ribs, which are typically about 1 centimeter to the left of the sternal margin. The pericardium is shown for illustration as well, with the pacing electrode 590 and ITV 324 between the ribs and pericardium. In the example shown, the pacing electrode 590 lies to the left of the subcutaneous electrode assembly 586; that alignment may be reversed in other examples or, alternatively, the subcutaneous electrode 586 may lie directly over the ITV electrode 590.

Figure 7A:
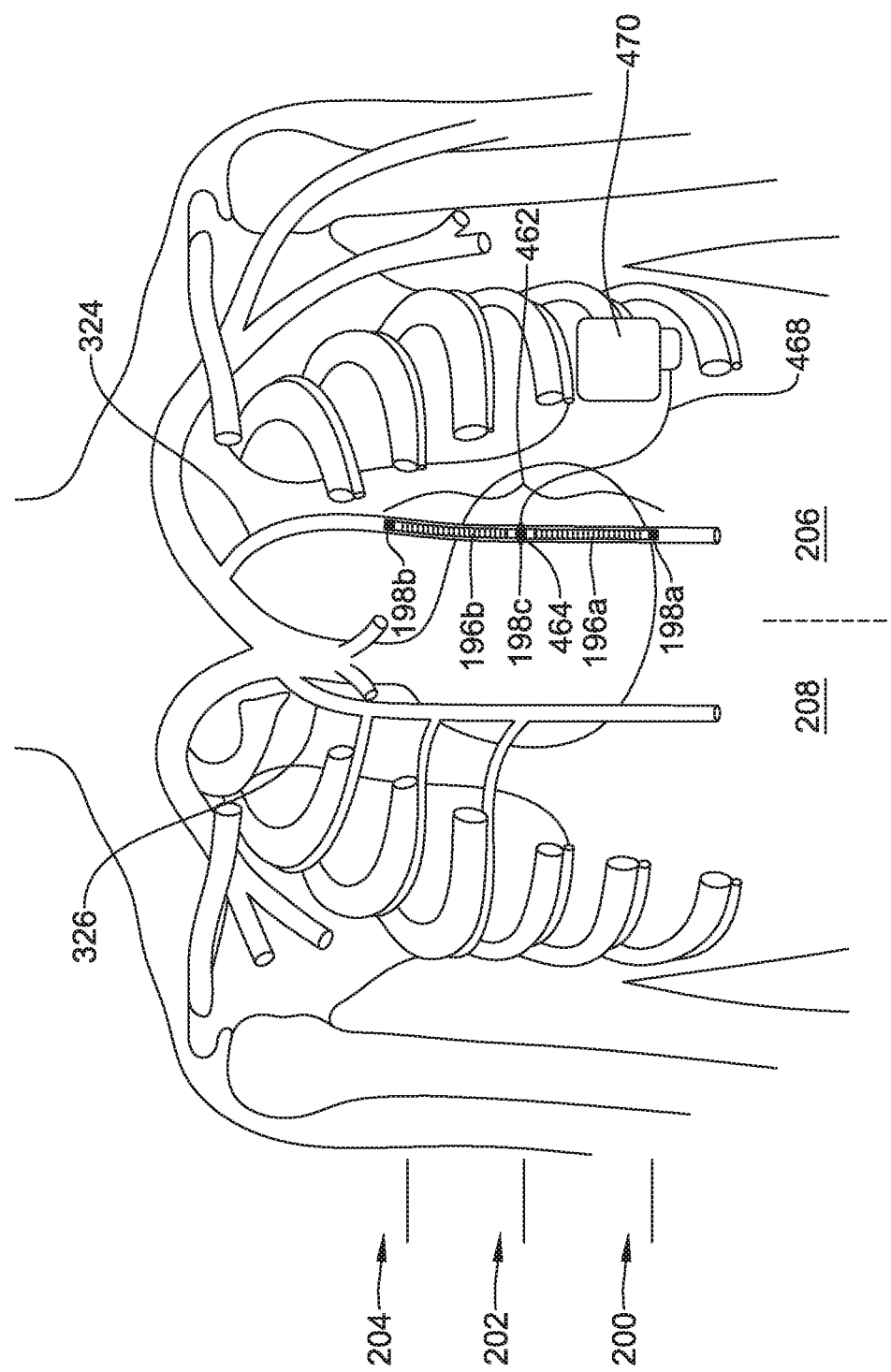
FIG. 7A shows parasternal implantation of a bifurcated lead in the left ITV.

In the example shown in FIG. 7A, a bifurcated multi-electrode structure 462 is implanted in the left ITV 324 parasternally through access location 464, in the middle region of the ribcage, such as between ribs 4 and 5 or between ribs 5 and 6. For placement, the left ITV 324 is accessed and a tunnel is established between the left axilla, where the canister 470 is implanted, and the access location 464. The canister 470 may be placed as desired, for example at the anterior axillary line, the midaxillary line, or in the posterior axillary line. The canister 470 or pulse generator housing (the terms may be used interchangeably) may instead by placed elsewhere such as on the right side of the chest or in a subclavicular location.

The lead 468 may, in this case, be a bifurcated lead with two distal fingers. A first distal finger may include first coil 196A and first ring electrode 198A. A second distal finger may include second coil 196B and second ring electrode 198B. Electrodes 198A and/or 198B may instead be a tip electrode. A third ring electrode 198C may be located on the first or second distal finger adjacent the bifurcation point, or may be located on the lead 468 proximal of the bifurcation point. Electrodes 198A, 198B, 198C may serve as sensing electrodes. The coil electrodes 196A, 196B may also serve as sensing electrodes.

The first and second distal fingers may be separately addressable. In one example, the first and second distal fingers are identical to one another, allowing the physician ease of use and flexibility during implantation. In another example, the finger that extends superiorly is of larger outer diameter than the finger that extends inferiorly, as the ITV is larger at more superior locations. In the example shown, the first and second distal fingers have similar electrodes. In another example, different electrode structures are used on each, such as by providing smaller electrodes adapted to pacing and/or sensing on the distal finger that extends more superiorly, and a longer coil electrode on the distal finger that is to extend inferiorly.

Various designs or design features may be used to aid in maintaining a desired position for the lead 468, including tines, hooks, curvature or bias of the lead, and inflatable or expandable structures. In the illustration, a suture sleeve is shown at 566 and is used to fixate the lead 468, for example, to the subcutaneous fascia.

In the example shown in FIG. 7A, a left axillary canister location is shown; a right sided axillary, or a pectoral or subclavicular left or right position may be used instead, in combination with right or left ITV placement. The first and second coils 196A, 196B and canister 470 may serve as therapy delivery electrodes. As such there may be multiple therapy vectors such as between first coil 196A and second coil 196B, between either of first and second coils 196A and 196B and the canister 470, or between a combination of two of the three therapy electrodes 198A, 198B and canister 470, and the third such electrode 198C, such as by linking coils 196A and 196B in common as the anode or cathode relative to the canister 470.

These various electrodes 196A, 196B, 198A, 198B, 198C may be used for sensing cardiac signals in various combinations using, for example, methods and circuitry discussed in U.S. Pat. No. 7,783,340, titled SYSTEMS AND METHODS FOR SENSING VECTOR SELECTION IN AN IMPLANTABLE MEDICAL DEVICE USING A POLYNOMIAL APPROACH, and U.S. Pat. No. 8,483,843, SENSING VECTOR SELECTION IN A CARDIAC STIMULUS DEVICE WITH POSTURAL ASSESSMENT, and/or US PG Patent Pub. Nos. 2017/0112399, 2017/0113040, 2017/0113050, and 2017/0113053, the disclosures of which are incorporated herein by reference.

In addition, one or more of the ring or tip electrodes 198A, 198B, 198C may be used for therapy delivery. In an example, defibrillation therapy may use coils 196A, 196B coupled in common as the opposing pole to the canister 470, while pacing therapy may use coils 196A and 196B as opposing electrodes for post-shock pacing therapy, with a still different combination of electrodes may be used to provide ventricular pacing therapy for example by pacing between coil 196B and tip electrode 198C.

This description of electrode utility is not intended to be limiting; other combinations and uses may apply for the coil and other electrodes; the coil(s) may be used for sensing, and the ring or tip electrodes may be used for therapy delivery. If desired, one or more sensing and/or therapy electrodes may take the form of a directional electrode that does not traverse fully around the circumference of the lead. The number of electrodes may be increased as desired, for example, 5 electrodes are shown; 8 or 16, or more, electrodes may be used if desired. For example, an 8 or 16 electrode lead (similar to those used in Neuromodulation systems, such as the Boston Scientific Corporation Infinion™ 16 Percutaneous Lead, featuring 16 electrode contacts, over a 67 mm Span; for cardiac purposes such a lead may be modified, for example, by using a wider inter-electrode spacing and/or different electrode surface area) may be used, with individual electrodes selected for sensing and/or pacing, while sets of electrodes may be ganged together for therapy delivery.

Line 202 is provided, illustratively, to separate the atria and ventricles. The lead 468 may be placed as shown such that the second coil 196B is about level with the atria, and first coil 196A is about level with the ventricles, if desired. In some examples fewer or different electrodes may be provided on the lead 468 such as by excluding one or the other of the first coil 196A or second coil 196B. Various designs are also shown herein.

Line 204 is provided to indicate the top of the heart, with the apex or bottom of the heart marked at 200. In some examples, one or more electrodes on the lead 468 are provided at or inferior to the apex 200, or at or superior to the top 204 of the heart. In the example shown, on the other hand, the electrodes are located generally between the apex 200 and top 204 of the heart.

The illustration shown in FIG. 7A places the lead on the left side 206 of the patient. In other examples, the right side 208 of the patient may instead or in addition be accessed, including the right ITV 326. Access to the right ITV 326 may be achieved by advancing a guide catheter and/or guidewire through a parasternal access position adjacent the right side of the sternum.

Figure 7B:
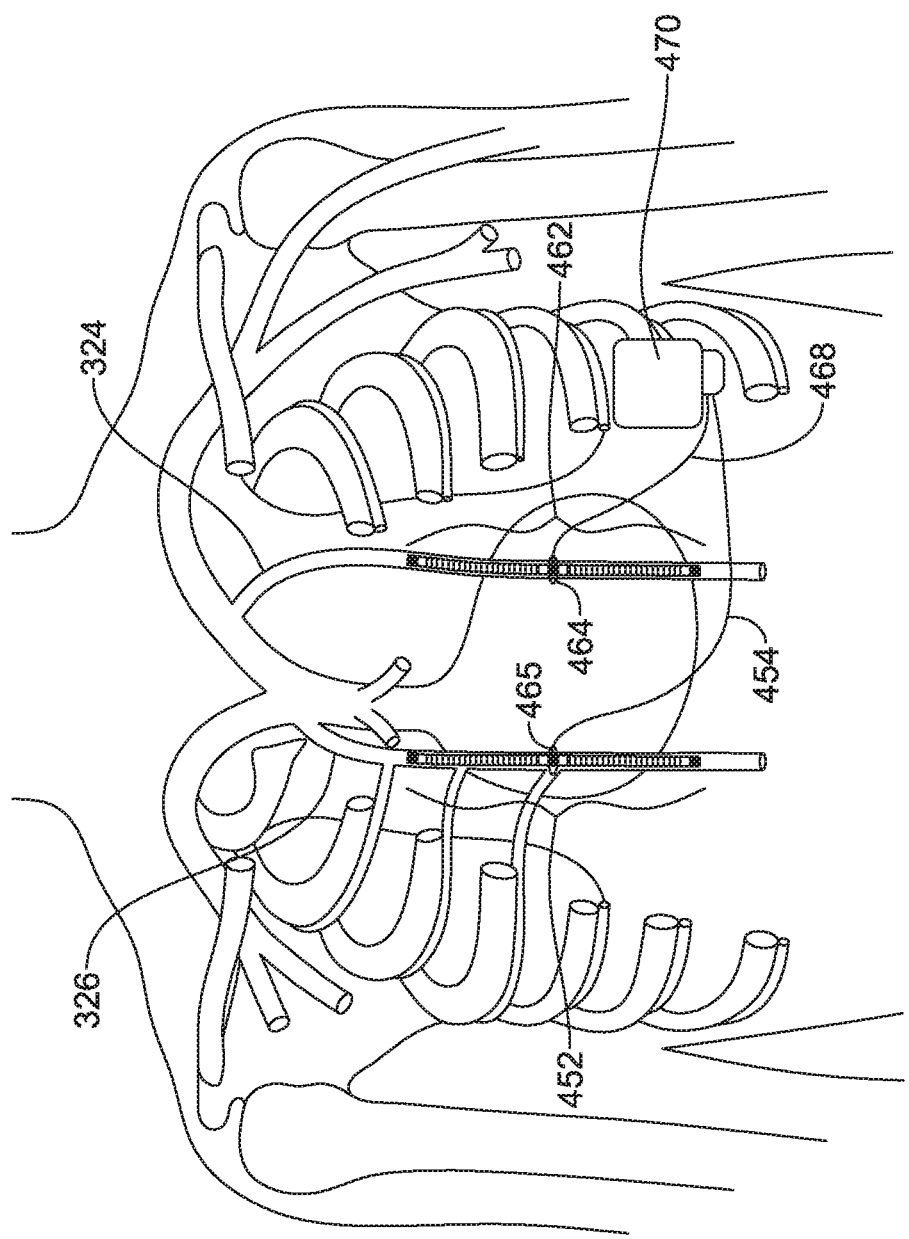
FIG. 7B shows parasternal implantation of a bifurcated lead in each of the left and right ITVs.

In some examples, each of the left and right ITV 324, 326 may receive a lead. The lead may be split into first 454 and second 468 portions, as shown in FIG. 7B, and a yoke may be provided near the canister 470 to join two leads together, or a header on the canister 470 may be configured to receive more than one lead 454, 468, if desired, to provide leads in each of the left and right ITV 324, 326. If two leads are provided, one lead may be in the right ITV with another lead in the left ITV, or both leads may be for implantation in one ITV using superior, inferior, parasternal or intercostal access. For example, pacing between right and left side lead placements may be performed to target specific chambers or chamber combinations, or sensing may be performed using one pair of electrodes with therapy delivery using a different pair of electrodes to achieve resynchronization or other desirable effect.

FIG. 7B shows implantation of bifurcated electrode structures from locations 464, 465 in both ITVs. In this example, the right ITV 326 is shown with the bifurcated electrode structure 452 on lead 454 disposed therein. A second lead 468 enters the left ITV 324 with a bifurcated electrode structure 462 disposed therein. Alternatively, a single lead extending from the canister 470 and then branching into first and second lead branches may be used. A canister 470 for the system is shown implanted in the left axilla. As discussed above, the canister 470 may alternatively be implanted in a right sided axillary, pectoral or subclavicular left or right position. As noted above, the parasternal access locations 464, 465 to each of the left and right ITV 324, 326, may be in the middle region of the ribcage, such as between ribs 4 and 5 or between ribs 5 and 6. Other access locations into the ITVs may be used if desired, such as at access locations 345, 340, 342, 335, 344, or 337 shown in FIG. 4.

In another example, a sensing electrode for p-wave sensing may be implanted in the right ITV and a pacing/defibrillation therapy electrode may be implanted in the left ITV. The implanted device may communicate the p-wave information to a leadless device(s) for the purposes of ventricular pacing with atrial tracking (VDD). When electrodes are placed in both the left and right ITV, any combination and orientation of sensing, pacing, and defibrillation electrodes may be used, depending on the desired sensing and pacing. For example, placement of electrodes in the right ITV may be desired for multiple pacing electrodes in a superior location to cover the right atrium.

Further, placing one or more pacing electrodes in an inferior location may be desired to cover the right ventricle for therapy (or sensing) purposes. Alternatively, a defibrillation coil electrode may be used in this location. In some examples, electrodes positioned to sense the p-wave may be desired to time pacing of the right ventricle either from the ITV or from another lead or leadless device placed in the right ventricle or elsewhere in or near the heart. The above examples apply equally to the left ITV, with multiple electrodes positioned in superior positions for left atrial sensing and/or pacing. Multiple electrodes placed in inferior positions may be used for left ventricular sensing and/or pacing, and a coil defibrillation electrode may be desired in these locations for defibrillation. FIGS. 12-16 illustrate some exemplary configurations of electrodes, however these are understood to be non-limiting.

Figure 8:
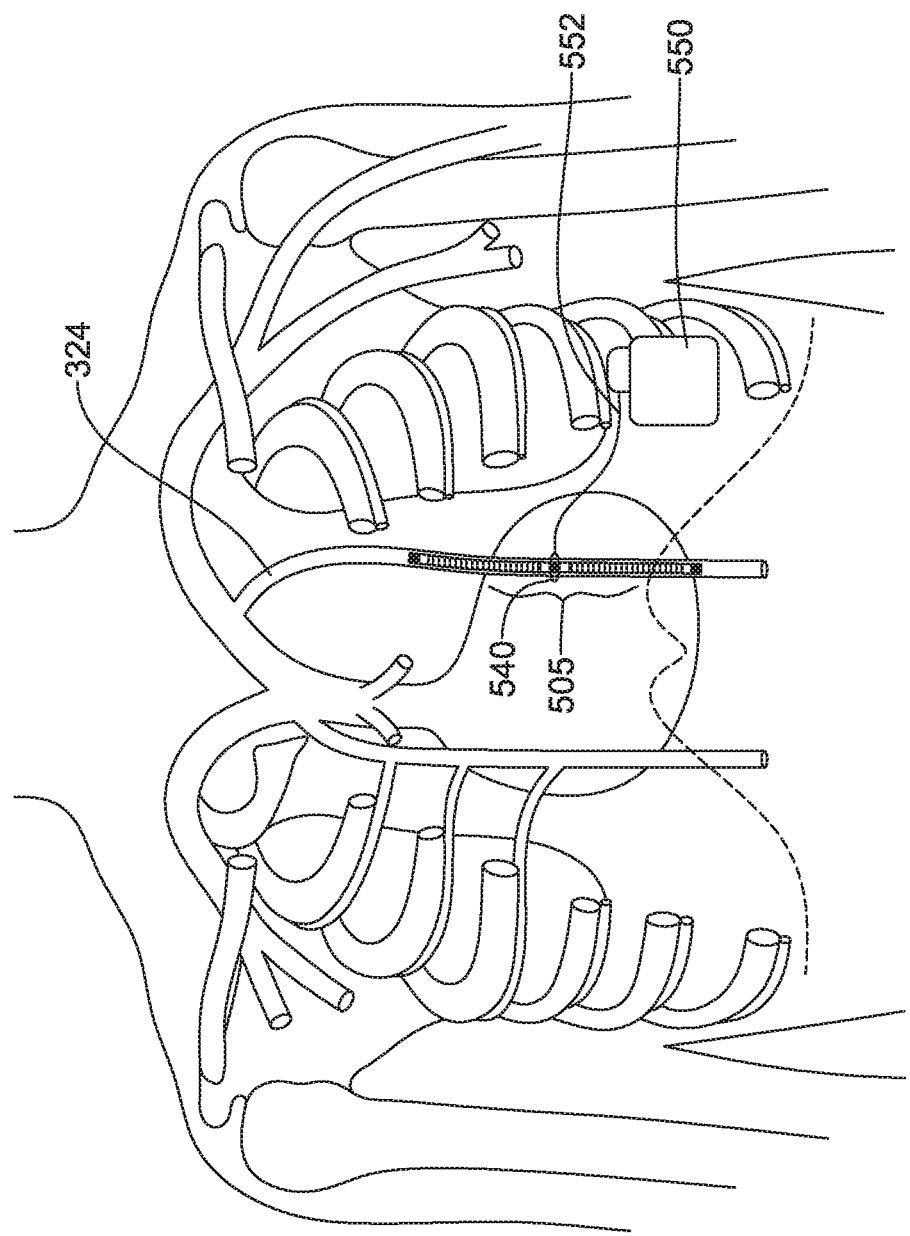
FIG. 8 shows parasternal implantation of a bifurcated lead in the left ITV.

FIG. 8 shows a bifurcated electrode implanted parasternally via an access location 540 in the left ITV 324. The lead 552 includes a bifurcated electrode structure 505 which may be inserted at a single access location 540, with a superior branch of the electrode structure inserted into the ITV in a superior direction and an inferior branch inserted in an inferior direction. The superior and inferior branches of the electrode structure may have the same structure or they may have different structures.

In some examples, a flexible bifurcated lead may be introduced with the support of a guidewire and sheath. After percutaneous access of the ITV via needle, a guidewire may be inserted through the needle and advanced superiorly through the ITV. The needle may be removed and an introducer sheath advanced over the guidewire. The superior leg of the lead may be passed through the sheath and into position, the sheath may be peeled back, and the guidewire retracted to the position where the guidewire entered the ITV. The guidewire may then be turned and advanced inferiorly through the ITV. A new sheath may be advanced over the guidewire, and the inferior leg of the lead may be passed through the sheath and into position. The sheath may then be peeled back and the guidewire removed, leaving the bifurcated lead with associated electrode structure in place within the ITV, as shown in FIG. 8.

In another alternative, one sheath may have a bifurcation, such that access may be generated by having a bifurcated sheath implanted over two guidewires going in opposing directions in the ITV. The guidewires may then be removed and the bifurcated lead implanted to track both directions in the sheath at once. Each arm of the bifurcated sheath may have a tear-away structure, such as a line of weakness, allowing sheath removal. A suture sleeve may be used to hold the arms of the lead in place, or to hold the lead itself proximal of a bifurcation location of the lead.

Figure 9A:
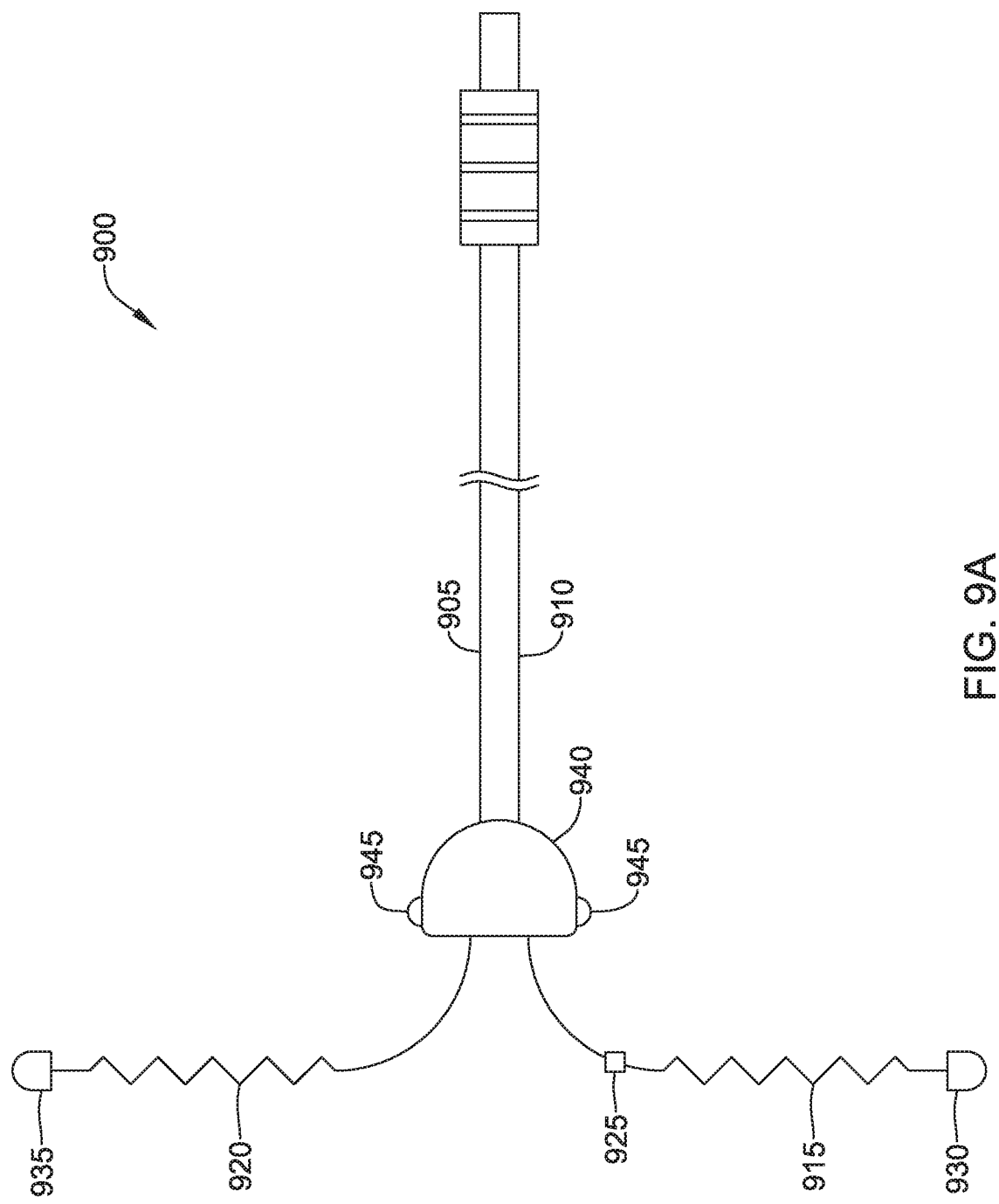
FIG. 9A illustrates a bifurcated lead design.

In some examples, two leads may extend from the canister to the electrode structure, with a first lead extending to the superior electrode and a second lead extending to the inferior electrode. In the example shown in FIG. 9A, the electrode structure 900 includes a first lead 905 and a second lead 910 extending from a canister (not shown) to the electrode structures. In this example, each lead of the electrode structure includes a high voltage coil 915, 920 and a terminal electrode 930, 935. The inferior lead includes a second electrode 925. The electrodes 925, 930, 935 may be any combination of pacing or sensing electrodes. Two or more electrodes and one or more coil may be located on each lead. The electrode structure 900 may include a connection element 940 which joins the superior and inferior leads 905, 910. The connection element 940 may include one or more structures to facilitate attachment to the underlying muscle tissue. The attachment structures may include suture loops 945 as shown in FIG. 9A. The connection element 940 may be a molded element connecting the first and second leads 905, 910, and the suture loops 945 may be molded into the connection element 940. Alternatively, the suture loops 945 may be separate structures attached to the connection element 940.

In an alternative, rather than two leads 905, 910, a single lead may extend to the connection structure 940, where the lead splits into two separate arms or fingers. However such a structure is less flexible surgically, as the relative lengths of the leads is not adjustable. In the example shown in FIG. 9A, the connection element 940 may couple two separate leads together, and may have, for example, a setscrew or other element to secure independently each of the leads 905, 910, allowing for adjustment of the length of lead distally of the bifurcation element.

Figure 9B:
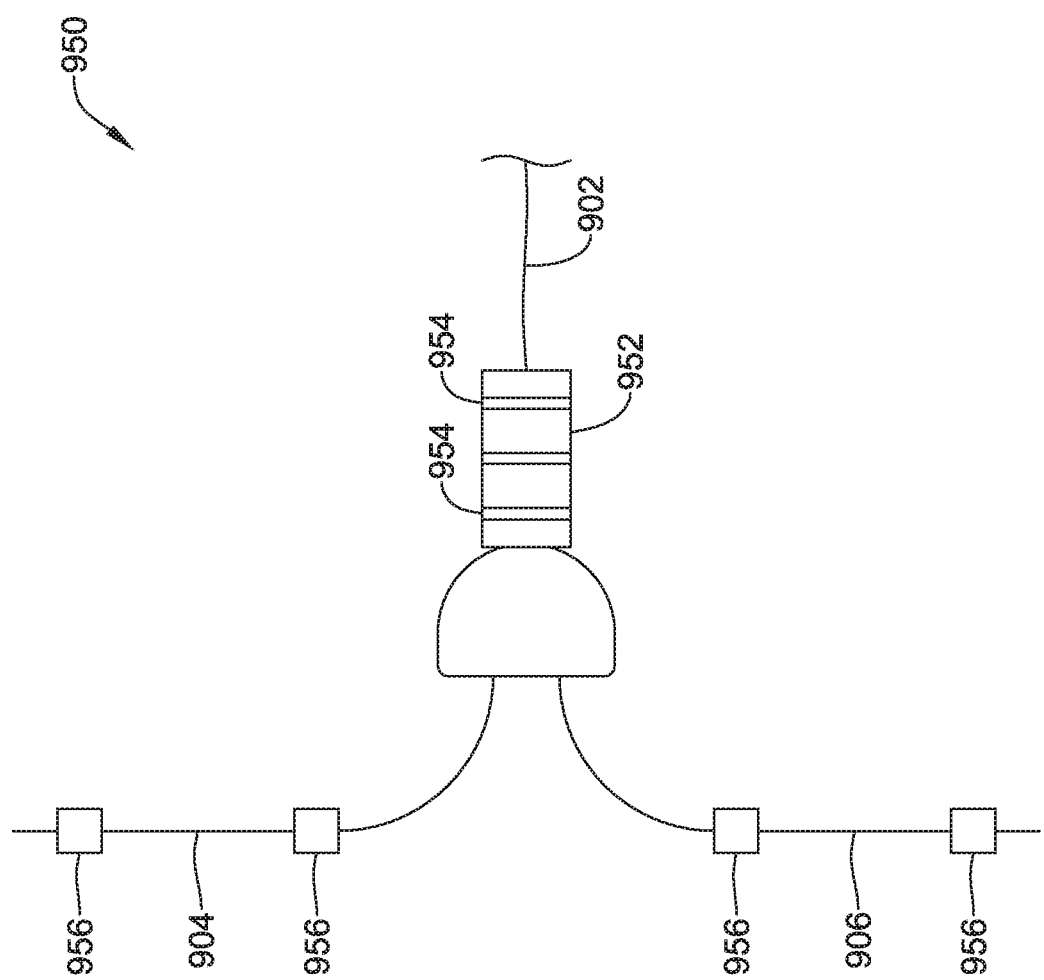
FIGS. 9B-9D illustrate various bifurcated lead designs.

In the example shown in FIG. 9B, a single lead 902 having the electrode structure 950 includes first and second fingers 904, 906 each having at least two electrodes 956, extending distally from a bifurcation element 942. The fingers 904, 906 are configured to extend in opposite directions distal of the bifurcation element 942, such that when implanted, the first finger 904 may extend superiorly and the second finger 906 may extend inferiorly within the same ITV. The electrodes may be any combination of pacing and sensing electrodes. In this example, an attachment structure in the form of a suture sleeve 952 is provided, with one or more grooves 954 configured to receive suture loops for attaching the electrode structure 950 to the underlying muscle tissue. The sleeve 952 may be a relatively short tubular structure extending a few centimeters or the sleeve 952 may extend to the canister and provide not only the suture attachment grooves 954, but also provide protection for the leads as they travel over the ribs to the canister. The sleeve 952 may be a molded tube with grooves 954 formed or carved therein.

Figure 9C:
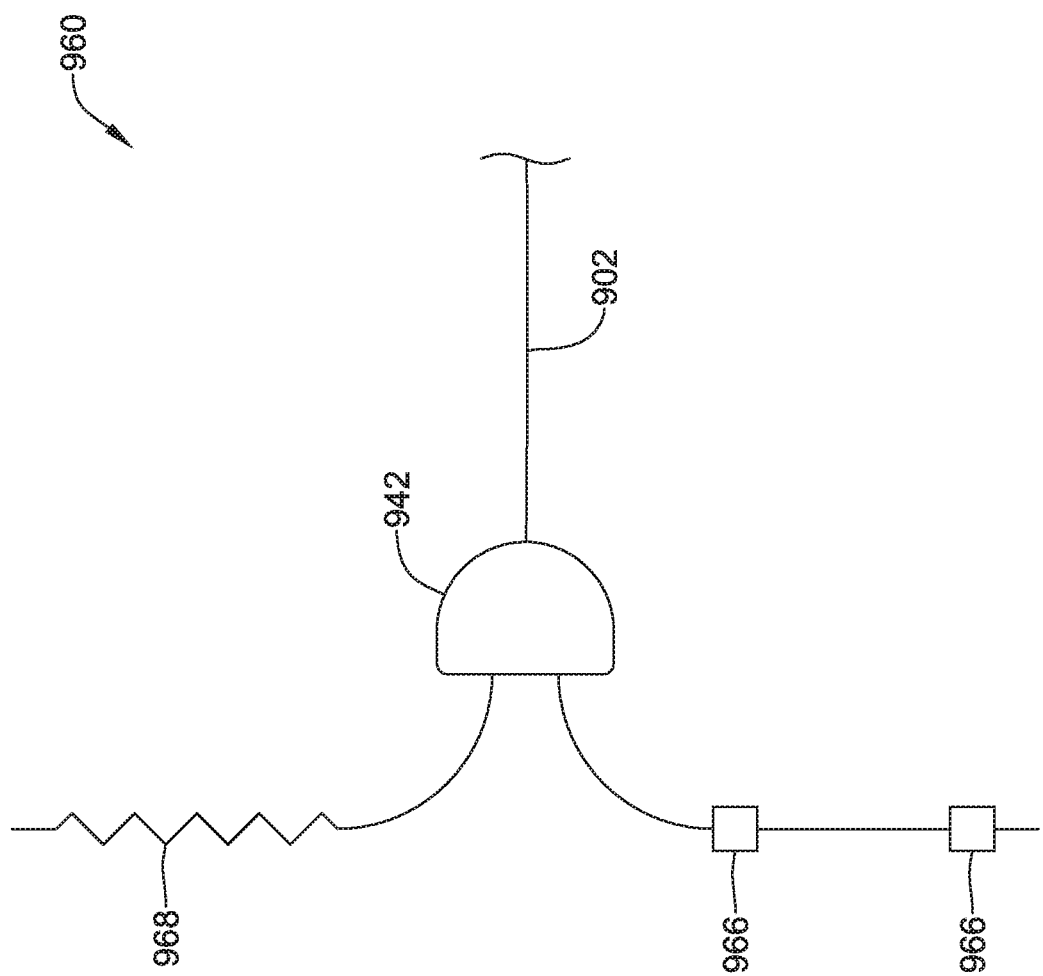
Figure 9D:
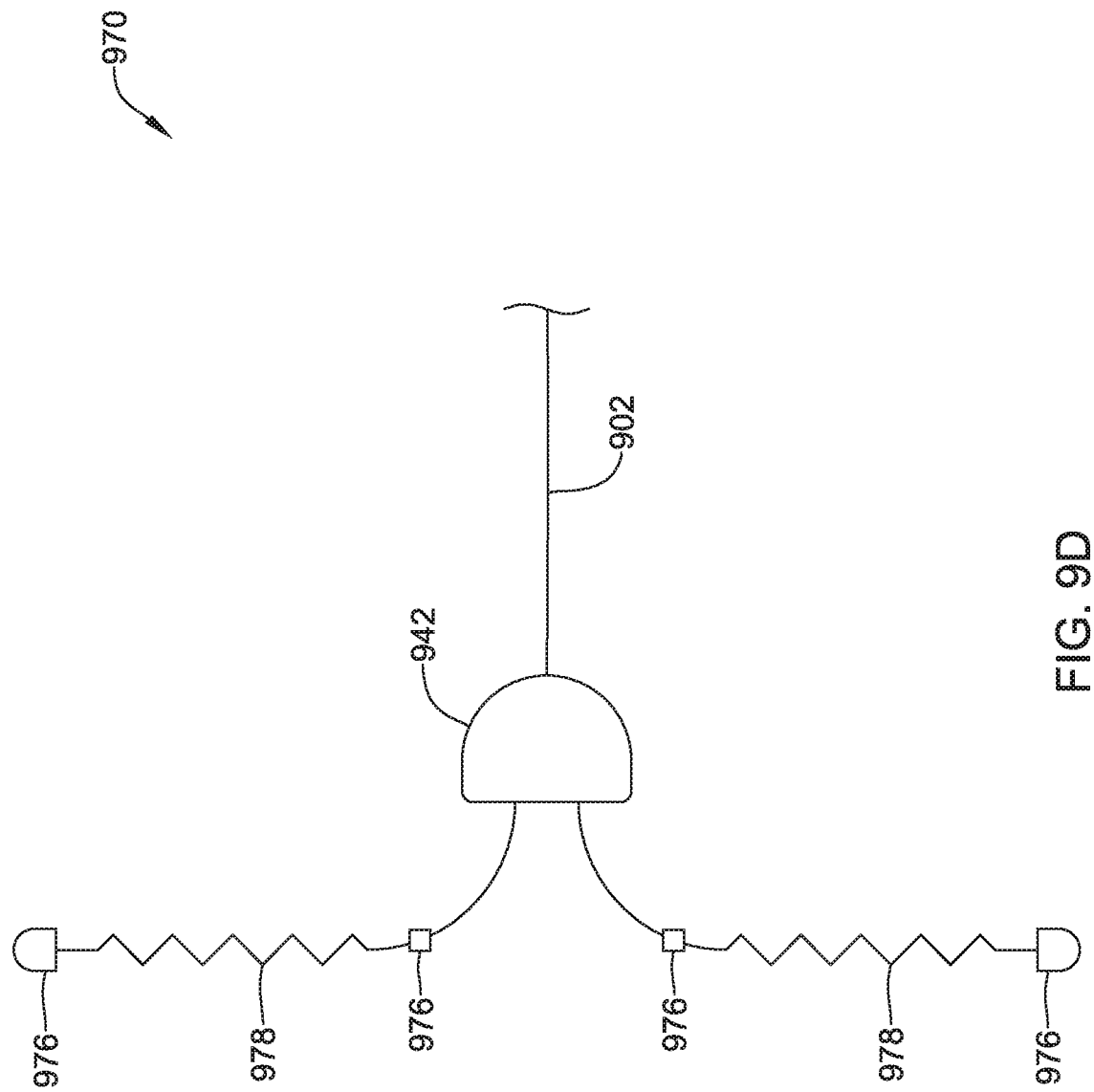

FIGS. 9C and 9D show further examples of bifurcated electrode structures. The electrode structure 960 shown in FIG. 9C has a high voltage coil 968 on the superior finger and two electrodes 966 on the inferior finger. The electrode structure 970 shown in FIG. 9D has a high voltage coil 978 between electrodes 976 on each of the superior and inferior fingers. The high voltage coils 978 may be common or separate, allowing for polarity programmability.

It will be understood that instead of the first and second leads 905, 910 shown in FIG. 9A, the structure may alternatively have a single lead extending proximally from a bifurcation structure and first and second fingers extending distally from the bifurcation structure, as shown in FIGS. 9B, 9C, and 9D. The electrodes 935, 920 shown on the first lead may be located on a first, or superior finger, and the electrodes 925, 915, 930 may be located on a second, or inferior finger. Similarly, for each of FIGS. 9B, 9C, and 9D, instead of the single lead 902 extending proximally from the bifurcation element 942 and the two fingers extending distally from the bifurcation element 942 as shown, two separate leads 905, 910 may be coupled at a connection element 940, as in FIG. 9A, with the first lead 905 having the superior electrode structures as shown in FIGS. 9B, 9C, and 9D, and the second lead 910 having the inferior electrode structures as shown in FIGS. 9B, 9C, and 9D.

In other examples, a single lead may extend from the canister to a bifurcation region, and two separate leads may extend from the bifurcation region, one to the superior portion of the electrode and one to the inferior portion of the electrode. The lead and electrode structures may have various sizes. For example, the transvenous portions of the lead and electrode structures may be 7 Fr or less. The lead portions extending from the bifurcation point to the canister may be larger, for example 9 Fr or greater, may be stiffer than the transvenous portion, and may include insulation and/or be reinforced to withstand compressive forces that may be encountered over the ribs. In the example shown in FIG. 9B, a sleeve 952 may surround the lead(s) from the canister to a location adjacent the entry point into the ITV.

Figure 10:
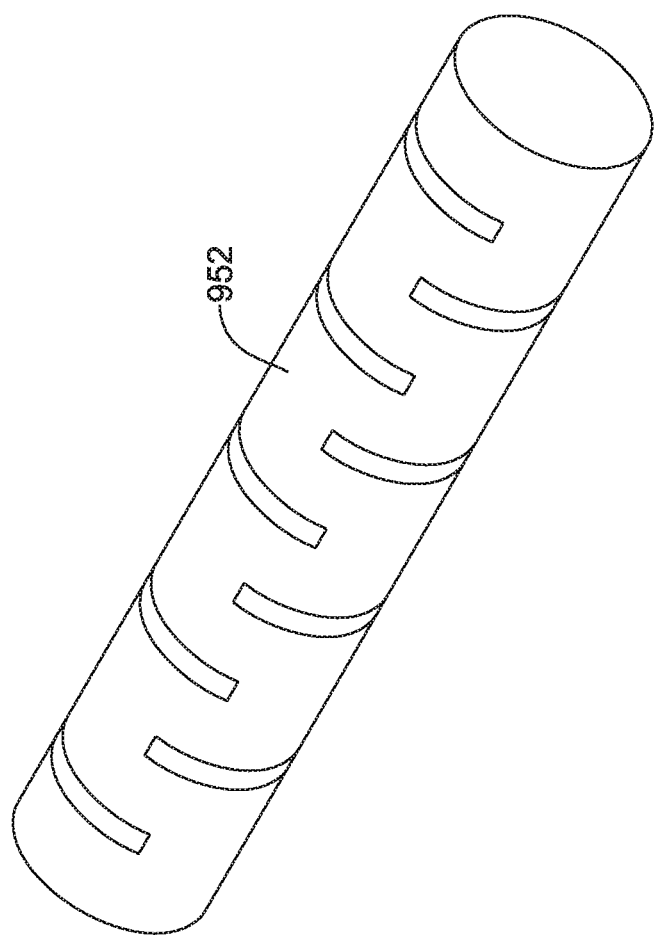
FIG. 10 shows a reinforcing tube.

The sleeve 952 may be a tube cut for flexibility, as shown in FIG. 10. The tube may be cut by laser, electrical discharge machining (EDM), or be cut mechanically, in any configuration of cuts to achieve a desired level of flexibility. The tube may be polymer such as PEEK, or metal, such as nitinol, titanium, stainless steel. Any suitable polymer, metal, or composite commonly used in medical devices may be used. The sleeve 952 may be molded and the leads inserted, or a covering such as polyurethane, polyisobutylene, or mixtures thereof may be extruded over the leads.

Figure 11:
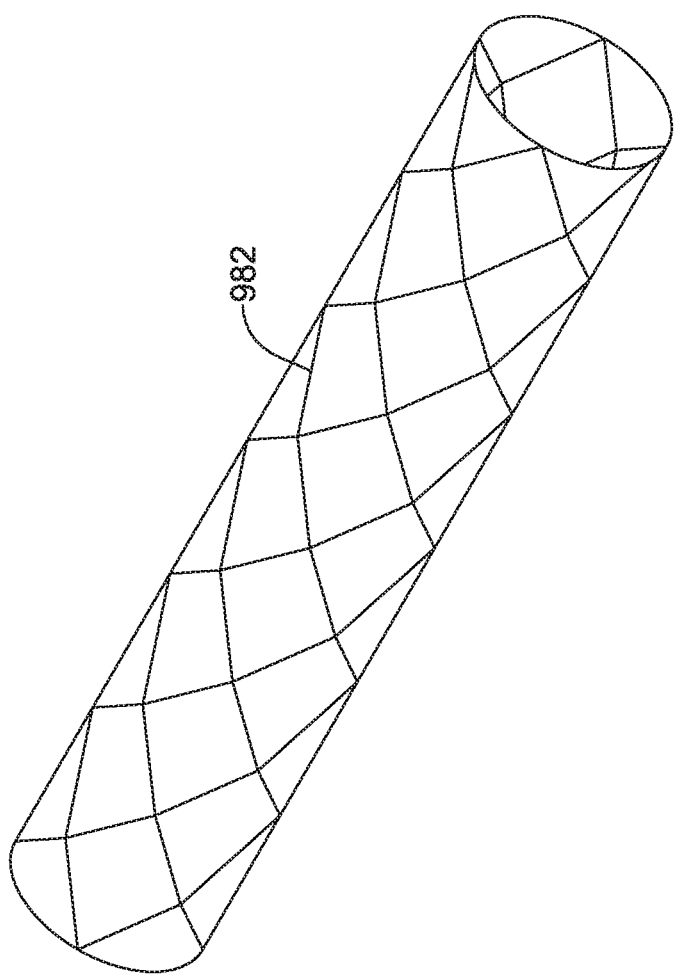
FIG. 11 shows a reinforcing braided structure.

Alternatively, the support/protective structure enclosing the leads may be a woven, knit, or braided structure 982, as shown in FIG. 11. The braided structure 982 may be formed from any conventional material used in making stents, and may be knit, woven, or braided using any method commonly used to make stents. Alternatively, a spray or sputter deposited coating may be applied to the leads. Inclusion of an outer support structure may further provide shielding for MRI safety purposes. It should be noted that any of the illustrative examples of leads may include MRI safety features such as current blocking nodes, loops or inductive elements, or specifically selected materials or other design features known in the art for MM safety/compatibility purposes. FIGS. 10-11 show single tube designs; in other example, a multi-lumen piece may be provides such as with side-by-side lumens to hold separate leads.

FIGS. 12-20 illustrate various lead designs. These leads may be manufactured of any suitable material and by any suitable manner. For example, numerous polymers are known for lead manufacture. Internal longitudinal or lateral support members, such as braids, core wires, etc. may be provided. Extrusion or molding may be used. Internal conductors may be formed of any suitable material (stainless steel, titanium, gold, silver, or any other conductive material may be used) and may take any suitable form, such as simple wires, coated wires, braided or wound wires, drawn wires, and/or drawn filled tubes, or other structures. The leads may include on all or a portion thereof various coatings such as an anti-microbial coating to reduce the likelihood, severity, and/or progression of infection. Some illustrative lists for such design details follow later in the disclosure.

Figure 12:
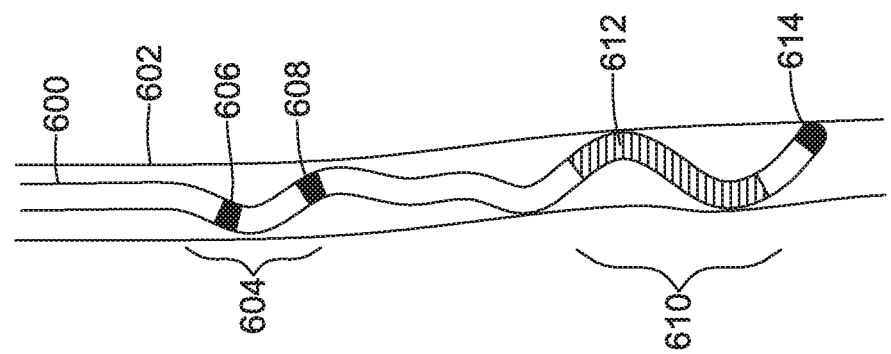

FIG. 12 shows an illustrative lead structure. A lead 600 is shown within a blood vessel 602, which may be an ITV. The lead may include ring electrodes illustrated at 606, 608, and a tip electrode 614, as well as a coil electrode at 612. Regions of curvature area shown at 604, and at 610. A single curvature may be provided instead. The curvature may be two-dimensional or three-dimensional. A two dimensional curvature may take the form, generally, of a zig-zag design, for example. Several embodiments may use a three dimensional curvature such as a pigtail or helix, for example.

In one example, the distal tip 614 is implanted inferior relative to the rest of the lead, such that the coil 612 is adjacent or level with the patient's ventricles. In another example, the distal tip is implanted superior relative to the rest of the lead, such that the coil 612 is adjacent or level with the patient's atria. In another example, the position of coil 612 is switched with the position of ring electrode 608, such that if implanted with the tip 614 superior relative to the rest of the lead, the tip 614 would be at about the level of the atria (or higher), while the coil 612 would be adjacent to or level with the ventricles.

Figure 13:
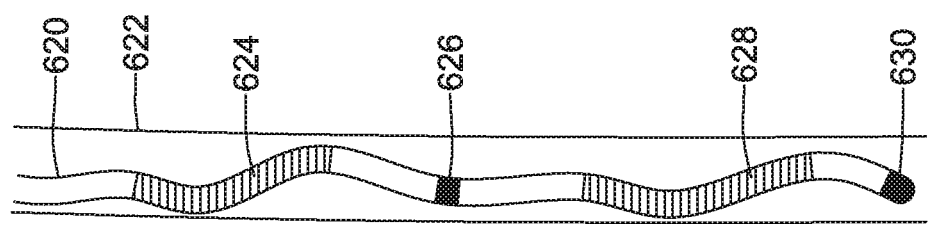

FIG. 13 shows another example. A lead 620 is shown within a blood vessel 622, which may be an ITV. The lead may include ring electrode 626 and a tip electrode 630, as well as coil electrodes 624, 628. An additional ring electrode may be placed proximal of the coil electrode 624, as shown above in FIG. 7A, if desired. With this example, the coils 624 may be spaced and positioned such that one is level with the ventricles and the other is level with the atria when implanted with the tip 630 either superior or inferior. As with FIG. 12, FIG. 13 shows that the lead has several areas of curvature.

In FIGS. 12 and 13, the curvature may be assumed by the lead in several ways. In an example, the lead includes a shape memory material and is generally straight and flexible until implanted in the body; after a few minutes to warm up, the shape memory material assumes the shape shown. In another example, a stylet is placed inside the lead during implantation to retain a generally straight shape, and the lead assumes the curved shape shown when the stylet is removed. In another example, an outer sheath is used to retain the lead until it is implanted with removal of the outer sheath allowing the lead to assume a desired shape. Combinations may be used as well; for example, a lead may include a shape memory portion or material or support structure, and may be implanted with the aid of a stylet and outer sheath to retain a low profile for implantation and then, once released by removal of the stylet and sheath, the shape memory material exerts forces to assume the shapes shown. Though not shown, curvature may be used for secure placement of any of the leads shown in FIGS. 14-20, if desired.

Figure 14:
FIGS. 12-20 show various lead designs.

FIG. 14 shows another example. Here, a lead 650 is shown inside a blood vessel 652, which may be the ITV. First and second ring electrodes are shown at 654, 656, and third and fourth ring electrodes are shown at 658, 660. Tines for fixation are shown at 662. The ring electrodes may be placed such that if the tines 662 are superior relative to the rest of the lead, electrodes 658, 660 would be level with the atria, and electrodes 654, 656 would be level with the ventricles. This may facilitate separate atrial and ventricular sensing and/or pacing channels. A coil electrode may also be provided. In one example, a lead as shown in FIG. 14 is implanted in the left ITV while a separate lead is implanted in the right ITV, with the right ITV comprising a defibrillation coil electrode, with an active canister defibrillator implanted in the left axilla. This approach would allow sensing (and optionally, pacing) directly over the heart using the ring electrodes 654, 656, 658, 660, with defibrillation delivered across the majority of the myocardium between the right-sided coil electrode and the left sided canister.

Figure 15:
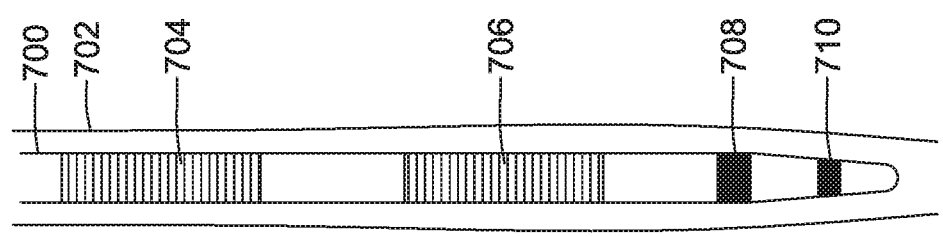

FIG. 15 shows another example. Here a lead 700 is implanted in a blood vessel 702 which may be an ITV. A first coil is shown at 704 and a second coil is shown at 706, with two distally located ring electrodes. If desired, the lead may taper as shown, though a fully cylindrical lead may be used instead. The taper may be useful during implantation to facilitate easier access through venous valves, particularly for insertions from superior to inferior, where the direction of insertion is counter to blood flow and hence valve structure. Curves or tines may be added, as well as other fixation features noted herein.

Figure 16:
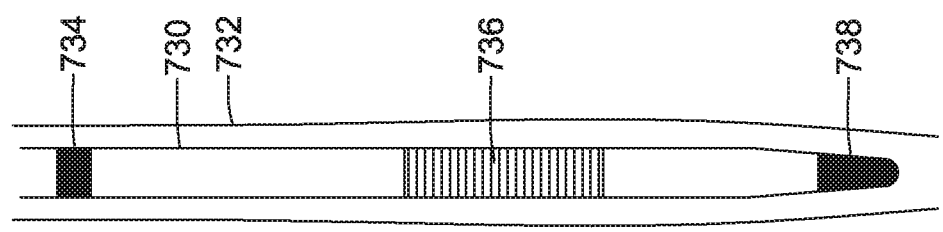

FIG. 16 shows another example. In this example, a lead 730 is shown inside of a blood vessel 732 which may be an ITV. A proximal ring electrode is shown at 734 and a coil at 736, with a distal tip electrode at 738. Curvature or tines may be added, as well as other fixation features noted herein.

Figure 17:
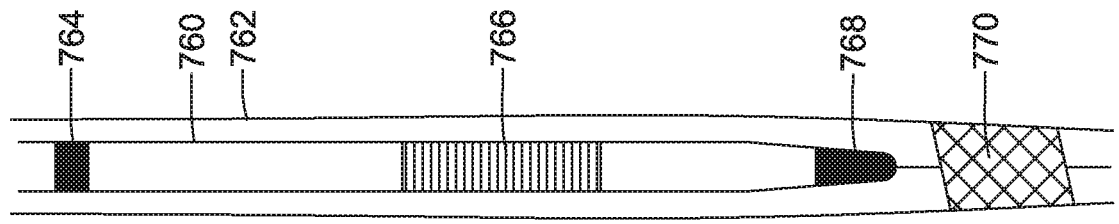

FIG. 17 shows another example. Here, the lead is much as in FIG. 16, with lead 760 shown inside a blood vessel 762 which may be a ITV, and with a proximal ring electrode 764, coil electrode 766, and distal tip electrode 768. However, now, an expandable member, such as a stent 770 is shown distal to the distal tip electrode 768. For example, a self-expanding stent 770 may be provided and carried within the distal tip electrode 768 until a desired position is reached for the stent 770. Such positioning may be determined using, for example, fluoroscopy. The proximal end of the lead may include a release mechanism, such as a control wire that can be advanced relative to the lead body, to push the stent 770 beyond the distal tip electrode 768 where it can then release. Self-expanding stents are well known in the art and may include, for example, spring-like structures. The stent 770 may include coatings designed to prevent thrombus from forming thereon and/or to encourage angiogenesis to best engage the venous wall. For removal, the connection to the stent 770 may be cut, for example, to leave the stent 770 in place as the rest of the lead is removed. Optionally the stent may be later removed using, for example, a stent retriever.

Figure 18:
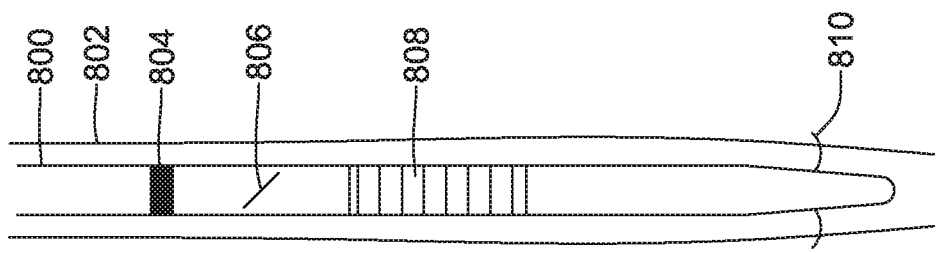

FIG. 18 shows another example. Here, a lead 800 is shown in a blood vessel 802 which may be an ITV. A proximal coil electrode is shown at 804. Distal of the proximal coil electrode (though any suitable location, more proximal or more distal, may be chosen), a side-engaging member is shown at 806. For example, engaging member 806 may be an arm, coil, hook, or tine that expands outward when actuated from the proximal end of the lead. Once the lead is in a desired position, engaging member 806 may be actuated to secure the lead in place.

The lead 800 is also shown with a coil electrode at 808. Finally, at the distal tip of the lead, a plurality of hooks are shown for engaging the walls of the blood vessel 802. The engaging member 806 or hooks 810 may be coated as desired for anti-thrombogenic or pro-angiogenic reasons, for example.

Figure 19:
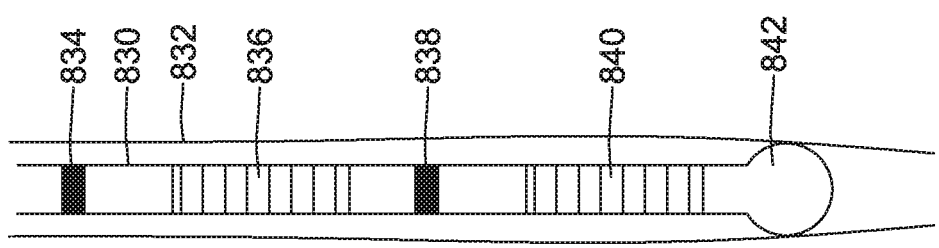

FIG. 19 shows another example. Here, a lead 830 is shown inside of a blood vessel 832 which may be an ITV. A plurality of electrodes are shown including a ring electrode 834, coil electrode 836, ring electrode 838, and coil electrode 840. At the distal end of the lead is an expandable member, such as a balloon 842, which may be inflated to secure the lead in place. It should be noted that the ITV is a blood vessel which, if occluded, will not necessarily cause harm to the patient as contralateral accommodation occurs readily. The balloon 842 may be expanded using inflation pressure, for example. A compliant or non-complaint material may be used the balloon. Rather than a balloon, an expandable sponge-type member that increases in volume once sufficiently wetted may be used instead.

Figure 20:
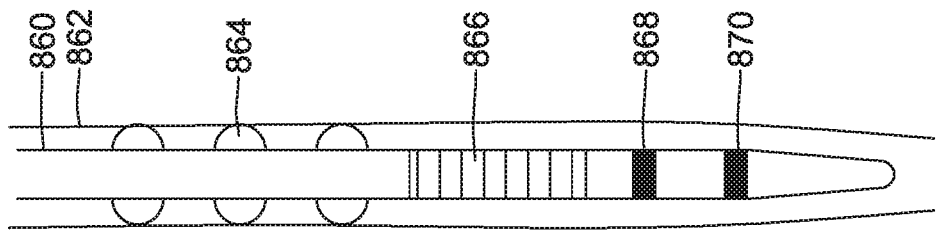

FIG. 20 shows another example. In this example, the lead 860 is shown in a blood vessel 862 which may be an ITV. This example includes a plurality of lobes 864 which hold the lead 860 in place inside the blood vessel 862. For example, the lobes may self-expand on removal of an outer delivery sheath or catheter, or the lobes may be expanded by movement of an outer shell of the lead relative to an inner shell. A coil electrode is shown at 866 and ring electrodes are shown at 868, 870.

The examples of FIGS. 12-20 are merely illustrative. Some examples may omit any fixation on the portion of the lead that extends into the blood vessel, and may instead rely on fixation using a suture sleeve subcutaneously placed as shown in certain of the above examples. In some examples, a relatively stiff lead may be used, as repeated flexion is not necessary when implanted in the ITV in the same manner as is the case inside the heart. A stiff lead is believed to be less likely to migrate.

In any of the above examples, additional electrodes may be included on the lead(s). While the examples illustrated may show four electrodes on a lead, it will be understood that additional electrodes, for example, five, six, seven, or eight electrodes may be placed on a single lead or lead finger of a bifurcated lead structure, and any combination of sensing and pacing/defibrillation electrodes may be included.

In any of the above examples, additional lead placement may take place. For example, an additional lead may be placed subcutaneously, within the heart, or in a different blood vessel such as the azygos vein. Additional device placement may occur as well, including, for example, the placement of a leadless cardiac pacemaker in one or more chambers of the heart.

The above examples facilitate a number of therapy options. For example, defibrillation therapy may be delivered in various configurations such as, without limitation:

Between a left ITV electrode or combination of electrodes and a right ITV electrode or combination of electrodes;
Between a left ITV electrode and a device housing placed in the left axilla or left subclavicular location;
Between a right ITV electrode and a device housing placed in the left axilla or left subclavicular location;
Between a left ITV electrode and a device housing placed in the right axilla or right subclavicular location;
Between left and right ITV electrodes electrically in common and a right or left axillary or subclavicular canister;
Between one ITV electrode and a second ITV electrode in common with a device canister in the left or right axilla or sublcavicular location;
Between a first electrode on a lead, and a second electrode on the same lead, where the first and second electrodes are in the same ITV;
Between a first electrode on a first finger of a bifurcated lead, and a second electrode on a second finger, where the first and second fingers are connected to the same bifurcated lead, where the first and second electrodes are in an ITV, such as in FIG. 7A.

In these examples, a "left ITV electrode" or "right ITV electrode" may include a single coil electrode or a combination of plural coils and/or one or more coils with one or more ring electrodes electrically in common. The above combinations may also be used for delivery of a bradycardia pacing therapy or an anti-tachyarrhythmia pacing therapy.

Further examples may provide a resynchronization therapy by delivering pacing pulses in various configurations, such as, without limitation:

In bipolar fashion within the left ITV to pace the left ventricle, and also in bipolar fashion within the right ITV to pace the right ventricle, with relative timing between the two sets of pacing therapies determined according to analysis of cardiac output or electrical response.
In bipolar fashion within one of the left or right ITV to stimulate a respective left or right ventricle in response to sensed signals in the left atrium (LA) and right atrium (RA) sensed with electrodes placed in an ITV at a superior location level with the atria.
In monopolar fashion between a device housing and one or both of left or right ITV electrodes, using for timing information atrial signals sensed using additional electrodes in at least one ITV and/or far-field sensed morphology detected using a device housing.

In an example, a heart failure or resynchronization therapy may be delivered as follows, with reference to FIG. 7A. A pacing therapy may be delivered by sensing atrial activity using two or three of the ring electrodes 198A, 198B, 198C shown in the bifurcated electrode structure 462 to determine timing for pace therapy delivery using the first and/or second coil electrode 196A, 196B and canister 470. Numerous other combinations may be had as can be seen to those skilled in the art.

Figure 21:
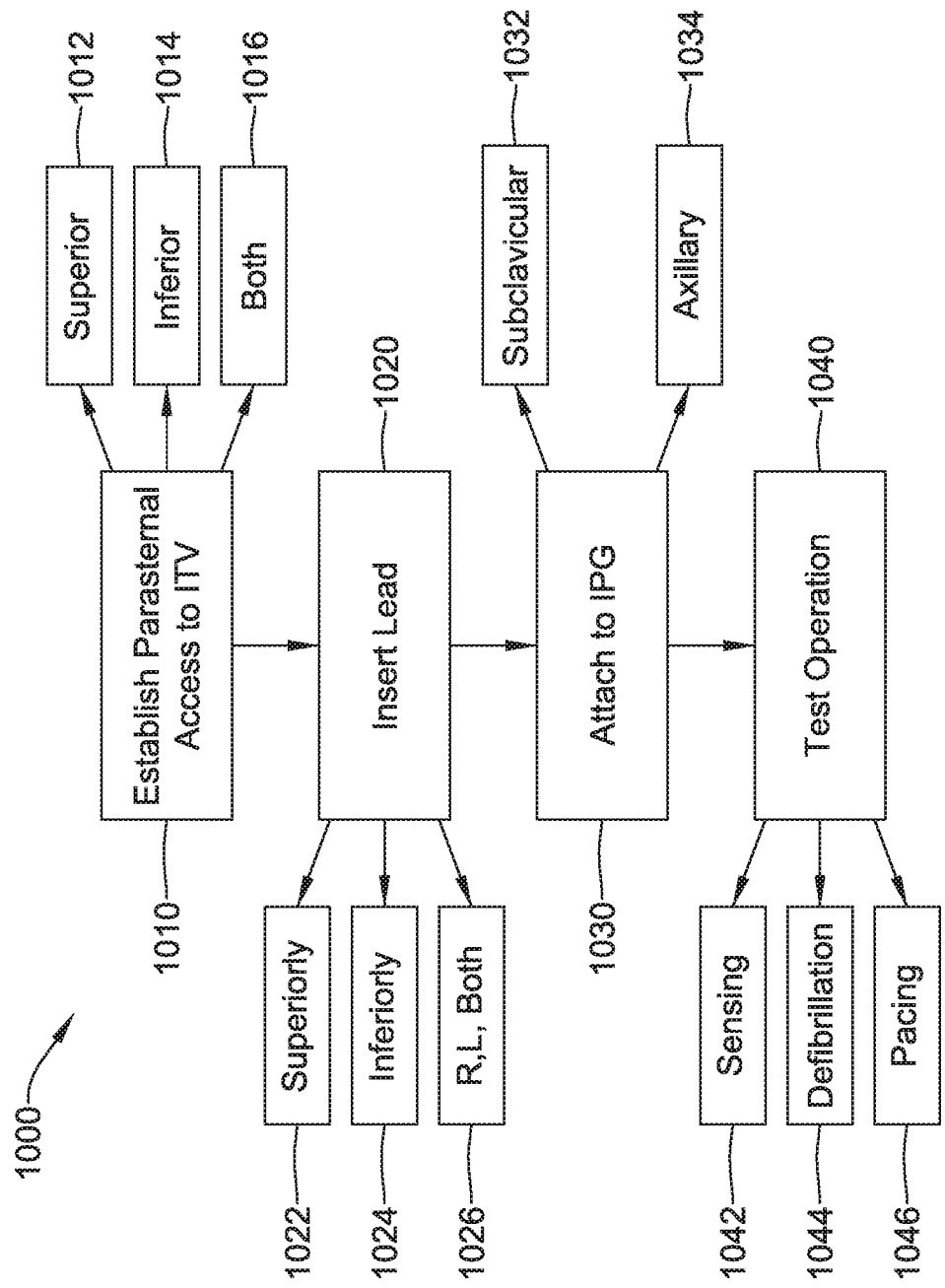
FIG. 21 is a block flow diagram for an illustrative method.

FIG. 21 is a block flow diagram for an illustrative method for providing a cardiac stimulus system to a patient. As shown at 1000, the method comprises establishing parasternal access to the ITV 1010, inserting a lead in the ITV 1020, attaching an implantable pulse generator (IPG) to the lead 1030, and performing test operations 1040.

For example, establishing parasternal access to the ITV 1010 may include accessing the ITV from a superior position 1012 such as between ribs 2 and 3 or 3 and 4. In another example, establishing access to the ITV 1010 may include accessing the ITV from an inferior position 1014 such as between ribs 4 and 5 or 5 and 6. In some examples, access via locations 1012, 1014 may include accessing both superior and inferior locations using a bifurcated lead structure 1016. In the above examples, establishing parasternal access to the ITV may include penetrating the intercostal space and entering the ITV using a cut-down method or a Seldinger technique.

In an example, inserting a lead 1020 may include insertion superiorly 1022, such as by starting parasternally from an inferior location 1014, and advancing the lead in a superior direction, as shown in FIG. 5. For another example, inserting a lead 1020 may include insertion inferiorly 1024, that is starting at a superior location 1012, and advancing the lead in an inferior direction, as shown in FIG. 6. In either such example, the right ITV, left ITV, or both ITV vessels may be used, as indicated at 1026.

Figure 22:
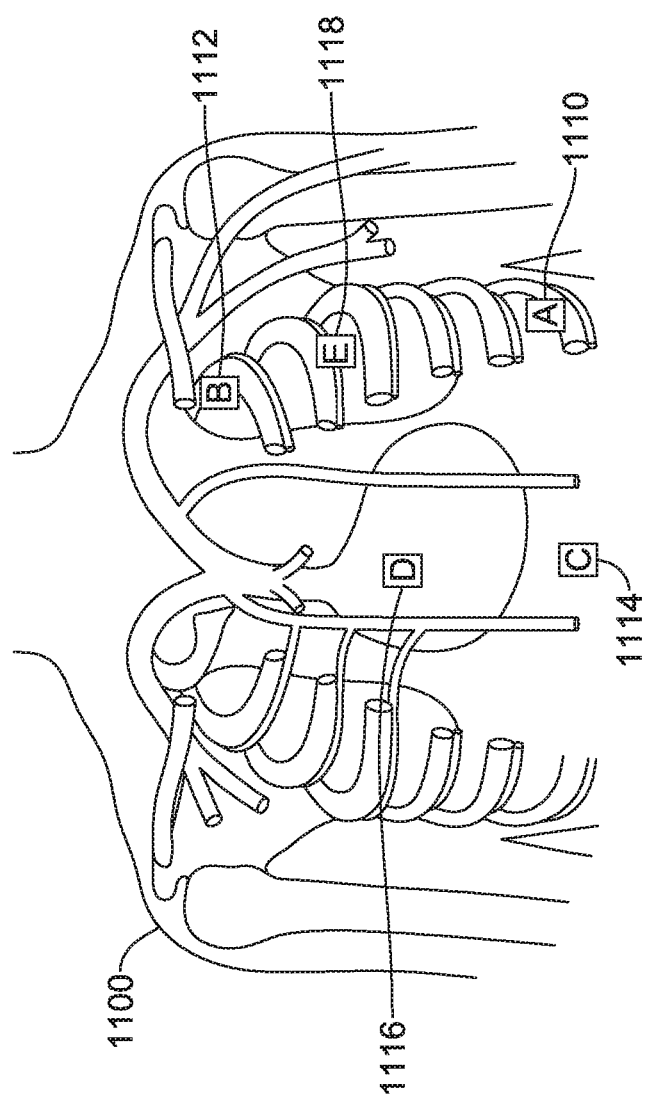
FIG. 22 shows several illustrative implant positions and combinations.
Figure 22:
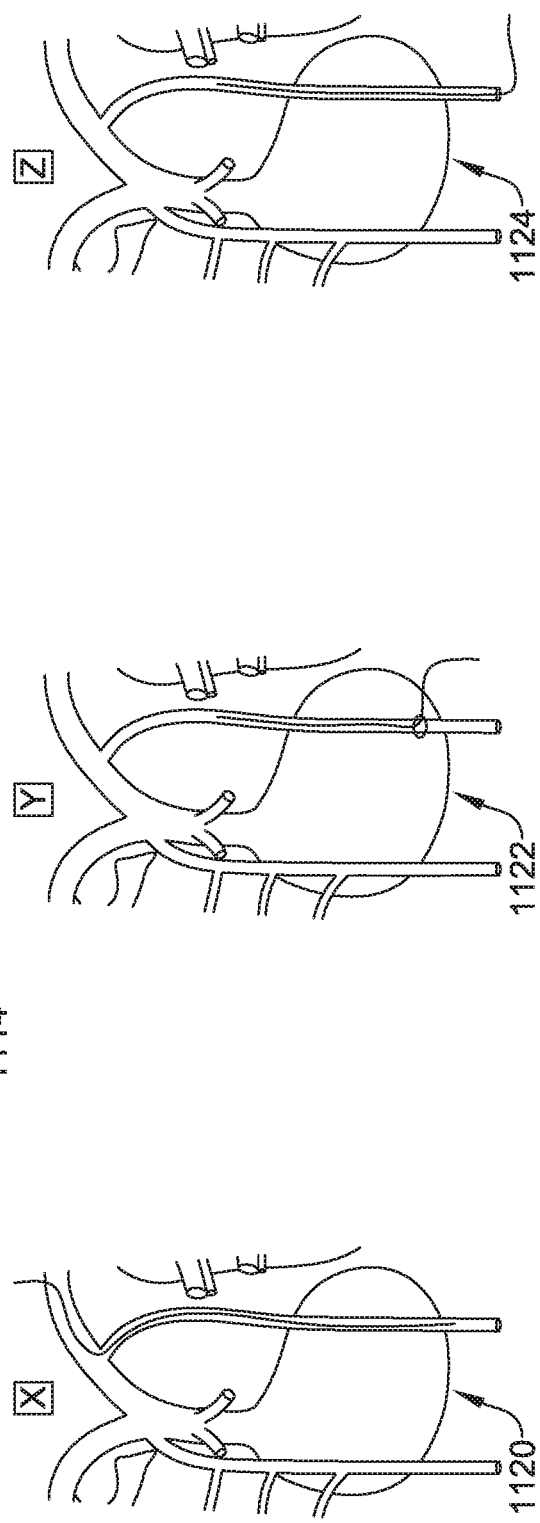

FIG. 22 illustrates a number of implantable positions and combinations. In the upper portion of the figure, a patient torso is shown at 1100. Illustrative positions for an implantable canister are shown at A, the left axilla 1110, B, a left clavicular position 1112, C, an abdominal position 1114, D, a suprasternal position 1116, and E, a costal position 1118. Illustrative placements for a left ITV lead are showing including X, access through the brachiocephalic vessel 1120, Y, parasternal access through an intercostal location 1122, and Z, access in the paraxiphoid window 1124 which may be termed an access using the superior epigastric vein. Right sided positions A', B', and E' (not shown) may be used instead for the various canister locations A, B and E. Right sided positions X', Y', and Z' (not shown), may be used instead for the ITV leads X, Y and Z, and/or there may be leads in both right and left ITVs. A further example relative to position X may include having the access to the brachiocephalic vein cross the midline from right to left or left to right, such that, for example, a subclavicular vein access and entry to the braciocephalic vein from the left side could allow placement of a lead in the right ITV or both right and left ITV. Any of the ITV lead positions may include variants in which the lead then passes into the mediastinum after entry to the ITV, or may include passage from the ITV into an intercostal vein, or passage into the ITV from an intercostal vein.

Thus combinations may be, for example:

Any one of canisters A, A', B, B', C, D, E, or E' with any one of leads X, X', Y, Y', Z, Z'.

Any one of canisters A, A', B, B', C, D, E, or E' with any one of leads X, Y, or Z and any one of X', Y', or Z'.

More particularly, the following are thought to be quite practical implementations:

A or A' with Y, Y', Z, Z', Y and Y', or Z and Z.

B or B' with X, X', or X and X', including wherein an access for X or X' crosses the patient's midline to provide right ITV lead implant from left side access or left ITV lead implant from right side access.

C with Y, Y', Z, Z', Y and Y', or Z and Z'.

D with Y, Y', or Y and Y'.

E with X, Y, or Z or, alternatively, a modified X crossing the midline to place in the right ITV from a left side access point, standing alone or in combination with either Y or Z.

E' with X', Y', or X', or, alternatively, a modified X crossing the midline to place in the left ITV from a right side access point, standing alone or in combination with either Y' or Z'.

Other positions may be used for the canister, such as, for example, looping the canister around to the posterior ribcage of the patient. It should also be noted that concomitant systems, such as an LCP or SICD may be placed as well, and that additional leads including additional subcutaneous, epicardial, transvenous, mediastinal/substernal, and/or intracardiac leads and electrodes may be included.

In various examples, either or both of the left or right ITV may be used for any of atrial pacing, ATP, and/or bradycardia pacing. For some patients, the right ITV may be more suited to atrial pacing as needed, though this may vary with anatomy and some systems will be capable of atrial pacing from the left ITV. Either ITV may be used as well for sensing atrial and/or ventricular activity. For many patients the right ITV may be preferable for P-wave sensing, though depending on anatomy, signal strength and system capability the left ITV may be used as well. It should be noted that statement regarding right and left ITV usage for various functions may not apply to patient with unusual physiological makeups, such as those patients having a more right sided heart. For example, a patient having hypertrophic cardiomyopathy may have the right ventricle more in contact with the left ITV than in other patients, adjusting the capability for chamber specific therapy by making the left ITV less "chamber-specific" to the left side of the heart than might otherwise be the case.

Pacing therapy may be delivered between two electrodes on one lead in a single ITV. Additionally or alternatively, pacing therapy may be delivered between electrodes on a first lead disposed in one of the left or right ITV, and a second lead disposed in the other ITV. Additionally or alternatively, pacing therapy may be delivered between an electrode in an ITV and an electrode disposed on a system housing/canister or on another lead disposed outside of the ITV such as subcutaneously, mediastinally, epicardially, in another blood vessel, or within the heart of a patient.

Chamber specific pacing may be possible as well. For example, in some patients the right ITV may be used to provide pacing therapy to the atria and/or right ventricle and the left ITV may be used to provide pacing therapy to the left ventricle. Again such usage may vary with patient anatomy. Chamber specific pacing may be delivered by using two electrodes in a single ITV and/or by steering therapy output to a particular chamber by selection of an electrode on one lead in an ITV and an electrode on a second lead, in the ITV and/or elsewhere such as on a housing or canister, subcutaneously, mediastinally, epicardially, in another blood vessel, or in the heart, for example. Such steering may be performed using a directional lead or a lead having a larger number of electrodes such as 8 or 16 and, if desired, by using a current steering technique to designate select electrodes and electrode combinations to be anodes or cathodes in a current controlled therapy output using techniques such as in U.S. Pat. No. 6,909,917, the disclosure of which is incorporated herein by reference.

Other vessels and implanted lead locations may also be used (such as having a lead in the azygos vein, an intracardiac lead, a subcutaneous lead) or additional devices such as a separately implanted leadless cardiac pacemaker may be included as well. In a further example, one or more of the transverse veins that flow into the ITV may be used for placement of an electrode or lead. For example, upon accessing an ITV, a physician may further access and emplace a lead or electrode into one of the anterior intercostal veins which run along the intercostal spaces of the anterior chest.

In an example, attaching to an IPG may include attaching to a canister located in a subclavicular location 1032, historically a common place to put an implanted canister for a transvenous defibrillator or pacemaker. In another example, attaching to an IPG may include attaching to a canister located in an axillary position 1034, such as that used with the S-ICD System. Other IPG locations may be used. Attachment may be directly to the IPG or to a splitter, yoke, or lead extension, if desired.

In an example, test operation 1040 may be used to verify one or both of device functionality and efficacy. For example, sensing operations 1042 may be tested and configured to check for adequate signal availability, for example, or by setting gain, filtering, or sensing vector selection parameters. Defibrillation operations 1044 may be tested by inducting an arrhythmia such as a ventricular fibrillation to determine whether the device will sense the arrhythmia and, if the arrhythmia is sensed, to ensure that the device can adequately provide therapy output by delivering defibrillation at a preset energy. Defibrillation testing 1044 may include determining for a given patient an appropriate defibrillation threshold, and setting a parameter for therapy delivery at some safety margin above the defibrillation threshold.

Prior transvenous systems would typically deliver up to 35 Joules of energy at most, with storage of up to 40 Joules of energy, using peak voltages in the range of up to nearly 1000 volts. The S-ICD System can deliver up to 80 Joules of energy, with 65 Joules often used for in-clinic system testing, with a peak voltage in the range of 1500 volts. The ITV location may facilitate energy levels similar to those of traditional transvenous systems (5-35 Joules, approximately), or may be somewhat higher (5 to about 50 joules, for example), or may still be higher (10 to about 60 joules, for example). Pacing thresholds may also be closer to those for traditional transvenous systems than the more recent S-ICD System.

In an example, pacing testing operation 1046 may include determining which, if any, available pacing vectors are effective to provide pacing capture. If desired, parameters may be tested as well to determine and optimize settings for delivery of cardiac resynchronization therapy. This may include testing of pacing thresholds to optimize energy usage and delivery, as well as checking that adverse secondary effects, such as patient sensation of the delivered pacing or inadvertent stimulation of the phrenic nerve, diaphragm or skeletal muscles are avoided.

Some embodiments of the present invention may take the form of an implantation tool set configured for use in implanting a cardiac device, such as a lead, into an ITV. Some such embodiments may include an introducer sheath. Some such embodiments may include a guide catheter. Some such embodiments may include a guidewire. Some such embodiments may further include a tool set for performing a Seldinger technique to access a blood vessel percutaneously.

Some embodiments of the present invention take the form of an implantable cardiac stimulus device comprising a lead and an implantable canister for coupling to the lead, the implantable canister housing operational circuitry configured to deliver output therapy in the form of at least one of bradycardia pacing, anti-tachycardia pacing, cardiac resynchronization therapy, or defibrillation, using a lead implanted in an ITV and a canister implanted in a patient.

As used herein, a coil electrode may be a helically wound element, filament, or strand. The filament forming the coil may have a generally round or a generally flat (e.g. rectangular) cross-sectional shape, as desired. However, other cross-sectional shapes may be used. The coil electrode may have a closed pitch, or in other words, adjacent windings may contact one another. Alternatively, the coil electrode may have an open pitch such that adjacent windings are spaced a distance from one another. The pitch may be uniform or varied along a length of the coil electrode. A varied pitch may be gradual tapered changes in pitch or abrupt or step-wise changes in pitch.

A coil electrode may have a length L that is generally larger than a width W. Round, oval or flattened coil electrodes may be used. Coil electrodes may have a length in the range of one to ten centimeters. In an example, a coil having a six or eight centimeter length may be used. In another example, a lead may have two four centimeter coils. Coils and leads may be in the range of four to ten French, or larger or smaller, in outer profile.

Coils and leads may be coated. For example, a thin permeable membrane may be positioned over a shock coil or other electrode and/or other portions of the lead to inhibit or to promote tissue ingrowth. Coatings, such as, but not limited to expanded polytetrafluoroethylene (ePTFE) may also be applied to the coil and/or lead to facilitate extraction and/or to reduce tissue ingrowth. In some embodiments, one or more of the electrodes, whether coils, rings, or segmented electrodes, include a high capacitive coating such as, but not limited to iridium oxide (IrOx), titanium nitride (TiN), or other "fractal" coatings which may be used, for example, to improve electrical performance. Steroidal and antimicrobial coatings may be provided as well.

The various components of the devices/systems disclosed herein may include a metal, metal alloy, polymer, a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Some examples of suitable polymers for use in the leads discussed above may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS A), polycarbonates, ionomers, biocompatible polymers, other suitable materials, or mixtures, combinations, copolymers thereof, polymer/metal composites, and the like.

In at least some embodiments, portions or all of the accessory devices and their related components may be doped with, made of, or otherwise include a radiopaque material. Radiopaque materials are understood to be materials capable of producing a relatively bright image on a fluoroscopy screen or another imaging technique during a medical procedure. This relatively bright image aids the user of the accessory devices and their related components in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the accessory devices and their related components to achieve the same result.

Any guidewire, introducer sheath, and/or guide catheter design suitable for medical interventions may be used for accessing the venous structures discussed herein.

The implantable systems shown above may include an implantable pulse generator (IPG) adapted for use in a cardiac therapy system. The IPG may include a hermetically sealed canister that houses the operational circuitry of the system. The operational circuitry may include various elements such as a battery, and one or more of low-power and high-power circuitry. Low-power circuitry may be used for sensing cardiac signals including filtering, amplifying and digitizing sensed data. Low-power circuitry may also be used for certain cardiac therapy outputs such as pacing output, as well as an annunciator, such as a beeper or buzzer, telemetry circuitry for RF, conducted or inductive communication (or, alternatively, infrared, sonic and/or cellular) for use with a non-implanted programmer or communicator. The operational circuitry may also comprise memory and logic circuitry that will typically couple with one another via a control module which may include a controller or processor. High power circuitry such as high power capacitors, a charger, and an output circuit such as an H-bridge having high power switches may also be provided for delivering, for example, defibrillation therapy. Other circuitry and actuators may be included such as an accelerometer or thermistor to detected changes in patient position or temperature for various purposes, output actuators for delivering a therapeutic substance such as a drug, insulin or insulin replacement, for example.

Some illustrative examples for hardware, leads and the like for implantable defibrillators may be found in commercially available systems such as the Boston Scientific Teligen™ ICD and Emblem S-ICD™ System, Medtronic Concerto™ and Virtuoso™ systems, and St. Jude Medical Promote™ RF and Current™ RF systems, as well as the leads provided for use with such systems.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method of implanting a lead for use in a cardiac stimulus system in a patient, the lead having a proximal end and a distal end, with at least one electrode thereon; the method comprising:
   creating a subcutaneous tunnel from a first position in the patient to a second position in the patient and placing at least a first portion of the lead in the subcutaneous tunnel;
   inserting a second portion of the lead into an internal thoracic vein (ITV) to a desired parasternal location relative to the heart of a patient by accessing the ITV near the second position; and
   implanting an implantable pulse generator for use with the lead at the first position.

2. The method of claim 1, wherein accessing the ITV near the second position comprises:

inserting a needle into the ITV through an intercostal space between two ribs near the second position;

advancing a sheath into the intercostal space and into the ITV; and advancing the distal end of the lead through the sheath and into the ITV.

3. The method of claim 1, wherein accessing the ITV near the second position comprises:

making an incision through the patient's skin and accessing the ITV;

making an incision into the ITV through an intercostal space between two ribs of the patient; and advancing the distal end of the lead through the incision and into the ITV.

4. The method of claim 1 wherein the first position is near the left axilla of the patient.

5. The method of claim 4 wherein the step of creating the subcutaneous tunnel comprises tunneling from the left axilla to the xiphoid, and again from the xiphoid to superiorly to the second position.

6. The method of claim 5 wherein the first portion of the lead comprises at least one subcutaneous electrode, and the second portion of the lead comprises at least one ITV electrode.

7. The method of claim 6 wherein the implantable pulse generator comprises therapy output circuitry configured to use at least one subcutaneous electrode for defibrillation, and at least one ITV electrode for pacing.

8. The method of claim 7 wherein the implantable pulse generator comprises therapy output circuitry configured for delivery of:

defibrillation therapy using at least one subcutaneous electrode and a housing of the implantable pulse generator as output electrodes;

anti-tachyarrhythmia pacing therapy using at least one ITV electrode and a housing of the implantable pulse generator as output electrodes; and bradycardia pacing therapy using at least two ITV electrodes.

9. The method of claim 4 wherein the step of creating the subcutaneous tunnel comprises tunneling from the left axilla to the second position, generally along the inframammary crease.

10. The method claim 1, wherein the lead is a bifurcated lead with at least first and second electrodes disposed on first and second lead branches, wherein inserting the second portion of the lead into the ITV comprises advancing the first lead branch inferiorly and advancing the second lead branch superiorly.

11. The method of claim 10 wherein the first lead branch has a smaller outer diameter than the second lead branch, and the first and second lead branches include electrodes thereon that are separately addressable by the implantable pulse generator.

12. The method of claim 10 wherein the lead further comprises a connection element adapted to control the length of the first and second lead branches that extends into the ITV.

13. The method of claim 1 further comprising placing an anchoring device at the second position to hold the lead in place once implanted relative to each of the ITV and the subcutaneous tunnel.

14. The method of claim 1 wherein the step of placing at least a first portion of the lead in the subcutaneous tunnel is performed by pulling the proximal end of the lead through the subcutaneous tunnel from the second position to the first position.

15. The method of claim 14 wherein the step of pulling the proximal end of the lead is performed in a first part by pulling the proximal end of the lead from the second position to a location near the xiphoid of the patient, and in a second part by pulling the proximal end of the lead from location near the xiphoid to the first position, wherein the first position is in the left axilla and the second position is along the left side of the sternum superior to the xiphoid.

16. A method of treating a patient comprising delivering defibrillation therapy between a first electrode disposed on a lead and an implantable pulse generator, wherein:

the lead comprises a first portion disposed in a subcutaneous, parasternal position and a second portion that extends into an internal thoracic vein (ITV) of the patient; and the first electrode is disposed on the first portion of the lead.

17. The method of claim 16 further comprising sensing an arrhythmia prior to delivering the defibrillation therapy using at least one electrode disposed on the first portion of the lead.

18. The method of claim 16 further comprising delivering post-shock bradycardia pacing to the patient following the defibrillation therapy using at least one electrode disposed on the second portion of the lead.

19. The method of claim 16 wherein the implantable pulse generator comprises operational circuitry including sensing circuitry adapted use a sensing configuration to select electrodes to provide sensing inputs used to detect cardiac conditions of the patient, further comprising modifying a sensing configuration of the sensing circuitry to use electrodes on the second portion of the lead following the defibrillation therapy.

20. A method of implanting a lead parasternally for use in a cardiac stimulus system in a patient, the lead having at least one electrode thereon; the method comprising establishing access to an ITV through an intercostal space between two ribs, inserting a distal end of a lead into the ITV, advancing the lead to a desired location parasternally relative to the heart of a patient, and securing the lead in place.

* * * * *